United States Patent
Hetherington et al.

(10) Patent No.: US 11,889,850 B2
(45) Date of Patent: Feb. 6, 2024

(54) METHOD FOR REMOVING GLUCOSINOLATES FROM OILSEED MEALS

(71) Applicant: AGRISOMA BIOSCIENCES INC., Gatineau (CA)

(72) Inventors: Mark Hetherington, Saskatoon (CA); Travis Hoffman, Saskatoon (CA); Michael Lindenbaum, Beaconsfield (CA)

(73) Assignee: AGRISOMA BIOSCIENCES INC., Gatineau (CA)

( * ) Notice: Subject to any disclaimer, the term of this patent is extended or adjusted under 35 U.S.C. 154(b) by 11 days.

(21) Appl. No.: 17/243,695

(22) Filed: Apr. 29, 2021

(65) Prior Publication Data
US 2022/0015389 A1    Jan. 20, 2022

Related U.S. Application Data

(63) Continuation of application No. 15/558,153, filed as application No. PCT/CA2016/051401 on Nov. 29, 2016.

(Continued)

(51) Int. Cl.
| | |
|---|---|
| A23K 10/14 | (2016.01) |
| C12N 9/24 | (2006.01) |
| A23K 10/30 | (2016.01) |
| A23K 10/10 | (2016.01) |
| A23K 50/10 | (2016.01) |

(Continued)

(52) U.S. Cl.
CPC .............. *A23K 10/14* (2016.05); *A23K 10/10* (2016.05); *A23K 10/30* (2016.05); *A23K 40/00* (2016.05); *A23K 50/10* (2016.05); *A23L 5/25* (2016.08); *A23N 17/001* (2013.01);

(Continued)

(58) Field of Classification Search
CPC ......... A23K 10/14; A23K 10/30; A23K 40/00
See application file for complete search history.

(56) References Cited

U.S. PATENT DOCUMENTS

| | | |
|---|---|---|
| 2,987,399 A | 6/1961 | Goering |
| 3,106,469 A | 10/1963 | Mustakas et al. |

(Continued)

FOREIGN PATENT DOCUMENTS

| | | |
|---|---|---|
| CA | 1057114 A | 6/1979 |

OTHER PUBLICATIONS

Office Action for corresponding Argentina patent application No. 20160103681 dated Feb. 26, 2020, with English translation, six pages.

(Continued)

*Primary Examiner* — Stephanie A Cox
(74) *Attorney, Agent, or Firm* — Harness, Dickey & Pierce, P.L.C.

(57) ABSTRACT

A process to remove the glucosinolates of oilseed meals, such as *Brassica carinata* oilseed meals, is provided. In one embodiment, exogenous myrosinase is used to convert the glucosinolates to volatile isothiocyanate compounds, which can then be removed under conditions of mild heat and negative pressure. In another embodiment, heat and pressure are used to remove glucosinolates from *Brassica carinata* oilseed. The processed meals may contain less than 80% of their starting levels of glucosinolates and may be suitable for use in various applications, including as animal feeds.

12 Claims, 2 Drawing Sheets

Related U.S. Application Data

(60) Provisional application No. 62/262,032, filed on Dec. 2, 2015.

(51) Int. Cl.
    A23L 5/20      (2016.01)
    A23K 40/00    (2016.01)
    A23N 17/00    (2006.01)

(52) U.S. Cl.
    CPC ......... *A23N 17/004* (2013.01); *A23N 17/005* (2013.01); *A23N 17/007* (2013.01); *C12N 9/24* (2013.01)

(56) References Cited

U.S. PATENT DOCUMENTS

| | | | |
|---|---|---|---|
| 4,083,836 | A | 4/1978 | Anjou et al. |
| 4,244,973 | A | 1/1981 | van Megen |
| 4,496,598 | A | 1/1985 | Sakai et al. |
| 5,686,108 | A | 11/1997 | Pusateri et al. |
| 6,824,796 | B2 | 11/2004 | Pusateri et al. |
| 6,955,831 | B2 | 10/2005 | Higgs et al. |
| 7,303,770 | B2 | 12/2007 | Fahey et al. |
| 7,645,468 | B2 | 1/2010 | Schweizer et al. |
| 8,697,150 | B2 | 4/2014 | Ekanayake et al. |
| 8,784,856 | B2 | 7/2014 | Stevens et al. |
| 2002/0151733 | A1 | 10/2002 | Ulrich et al. |
| 2002/0193617 | A1 | 12/2002 | Ulrich et al. |
| 2003/0083512 | A1 | 5/2003 | Jakel et al. |
| 2005/0031768 | A1 | 2/2005 | Sakai et al. |
| 2010/0234569 | A1* | 9/2010 | Helling .............. A23J 1/14 426/656 |
| 2011/0245526 | A1 | 10/2011 | Ekanayake et al. |
| 2013/0040023 | A1* | 2/2013 | Thomas .............. B29C 48/911 426/272 |
| 2013/0101723 | A1* | 4/2013 | Verkoeijen ............ A23L 33/40 426/601 |

OTHER PUBLICATIONS

Office Action from corresponding Brazilian Application No. BR112018008829-3 dated Nov. 29, 2016 with English translation. (19 pages).
International Search Report and Written Opinion of the International Searching Authority issued in PCT/CA2016/051401, dated Feb. 13, 2017 ISA/CA.
Sehwag, S. S. et al.: "A brief overview: Present status on utilization of mustard oil and cake", Indian Journal of Traditional Knowledge, vol. 14(2), Apr. 2015, pp. 244-250.
S.K. Jensen et al.; The effect of heat treatment on glucosinolates and nutritional value of rapeseed meal in rats; Animal Feed Science and Technology vol. 53, Jan. 1, 2995.
Extended European Search Report dated Aug. 29, 2018.
Bell et al., A survey of variation in the chemical composition of commercial canola meal produced in Western Canadian crushing plants, Can. J. Anim. Sci. 71:469-480, Jun. 1991. (Year: 1991).
Borgen, Birgit Hafeld et al., "Removing the mustard oil bomb from seeds: transgenic ablation of myrosin cells in oilsee-ape (*Brassica napus*) produces Mineless seeds", Journal of Experimental Botany Advance Access published Mar. 10, 2010, pp. 1-15.
Shen, Lianqing et al., "Endogenous and exogenous enzymolysis of vegetable-sourced glucosinolates and influencing actors", Food Chemistry 119, 2010, Elsevier Ltd., pp. 987-994.
Borow, Meike et al., "Glucosinolate hydrolysis in Lepidium sativum—identification of the thiocyanate-forming protein", Plant Mol Biol, Springer Science and Business Media B.V., 2007, pp. 1-13.
Anderson-Hafermann, J. C., et al., "Effects of Processing on the Nutritional Quality of Canola Meal", Poultry Science 12, 1993, pp. 326-333.
Aumaitre, A. et al., "Effect of Graded Levels of Raw and Processed Rapeseed on Feed Digestibility and Nutrient Utilization in Young Pigs", Animal Feed Science and Technology 24, 1989, pp. 275-287.
Bellostas, Natalia, et al., "Qualitative and quantitative evaluation of glucosinolates in cruciferous plants during their life cycles" Agroindustria 3(3), 2004, pp. 5-10.
Berhow, Mark A. et al., "Optimized analysis and quantification of glucosinolates from Camelina sativa seeds by reverse-phase liquid chromatography." Industrial Crops and Products 43, 2013, pp. 119-125.
Blackshaw, Robert E et al., "Alternative oilseed crops for biodiesel feedstock on the Canadian prairies", Can J. Plant Sci. 91, 2011, pp. 889-896.
Bones, A. M., "Distribution of beta-thioglucosidase activity in intact plants, cell and tissue cultures and regenerated plants of *Brassica napus* L", Journal of Experimental Botany, vol. 41, No. 227, Jun. 1990, pp. 737-744.
Bouaid, Abderrahim et al., "Pilot plant studies of biodiesel production using *Brassica carinata* as raw material", catalysis Today 106, 2005, pp. 193-196.
Branca, Ferdinando et al., Chapter 2 *Brassica*, Wild Crop Relatives: Genomic and Breeding Resources, Oilseeds. C. Kole. Berlin Heidelberg Springer-Verlag, 2011, pp. 17-36.
Cardone, Massimo et al., "*Brassica carinata* as an alternative oil crop for the production of biodiesel in Italy: Engine performance and regulated and unregulated exhaust emissions", Environ. Sci. Technol., 2002, pp. 4656-4662.
Cardone, Massimo et al., "*Brassica carinata* as an alternative oil crop for the production of biodiesel in Italy: Agronomic evaluation, fuel production by transesterification and characterization", Biomass and Bioenergy 25, 2003, pp. 623-636.
Cools, Katherine et al., "Comparative study between extraction techniques and column separation for the quantification of sinigrin and total isothiocyanates in mustard seed", Journal of Chromatography B, 901, 2012, pp. 115-118.
Drenth, A. C. et al., "Compression ignition engine performance and emission evaluation of industrial oilseed biofuel feedstocks camelina, carinata, and pennycress across three fuel pathways", Fuel 136, 2014, pp. 143-155.
Drenth, A. C. et al., "Fuel property quantification of triglyceride blends with an emphasis on industrial oilseeds aamelina, carinata, and pennycress" Fuel 153, 2015, pp. 19-30.
Dai, Ruyan et al., "Release of Allyl Isothiocyanate from Mustard Seed Meal Powder", Journal of Food Science, vol. 79, No. 1, 2014, pp. E47-E53.
Fahey, Jed W. et al. The chemical diversity and distribution of glucosinolates and isothiocyanates among plants, Phytochemistry 56, 2001, pp. 5-51.
Fenwick, G. R. et al., "Effect of Processing on the Antinutrient Content of Rapeseed." Journal Science Food Agriculture, 37, 1986, pp. 735-741.
Gasol, Charles M. et al., "Life cycle assessment of a *Brassica carinata* bioenergy cropping system in southern Europe", Biomass and Bioenergy 31, 2007, pp. 543-555.
Gasol, Charles M. et al., "LCA of poplar bioenergy system compared with *Brassica carinata* energy crop and natural gas in regional scenario", Biomass and Bioenergy 33, 2009, pp. 19-129.
Getinet, A., "The Inheritance of seed coat color in B. carinata A. Braun and an examination of seed quality parameters and their transfer from related species (*B. juncea* Czern & Coss and *B. napus* L.)", M.Sc. Thesis, Department of Crop Science and Plant Ecology, University of Saskatchewan, Saskatoon, 1986, 105 pages.
Getinet, A. et al., "Agronomic performance and seed quality of Ethiopian mustard in Saskatchewan", Canadian Journal of Plant Science 76, 1996, pp. 387-392.
Halkier, Barbara Ann et al., "Biology and biochemistry of glucosinolates", Annual Review of Plant Biology 57(1), 2006, pp. 303-333.
Henderson, H. M. et al., Effect of ascorbic acid on thioglucosidases from different crucifers, Phytochemistry vol. 11, 1972, pp. 3127-3133.
Kissen, Ralph et al., The 'mustard oil bomb': not so easy to assemble ?! Localization, expression and distribution of the components of the myrosinase enzyme system, Phytochemistry Reviews 8(1), 2009, pp. 69-86.

(56) References Cited

OTHER PUBLICATIONS

Mavromichalis, Ioannis, "The Maillard reaction in feed manufacturing", Feed Tech 5; 2001, pp. 13-14.

Marillia, Elizabeth-France et al., "Palliser's promise: *Brassica carinata*, An emerging western Canadian crop for delivery of new bio-industrial oil feedstocks", Biocatalysis and Agricultural Biotechnology 3(1), 2014, pp. 65-74.

Nagaharu, U., "Genome analysis in *Brassica* with special reference to the experimental formation of B. napus and peculiar mode of fertilization", Japan J. Bot. 7, 1935, pp. 389-452.

Prakash, Shyam et al. , "History, Evolution and Domestication of *Brassica* crops" In: Plant Breeding Reviews. Janick J. (ed), vol. 35, 2012, pp. 19-84.

Rask, Lars et al., "Myrosinase: gene family evolution and herbivore defense in Brassicaceae", Plant Molecular Biology 42, 2000, pp. 93-113.

Taylor, David C. et al., "*Brassica carinata* —A new molecular farming platform for delivering bio-industrial oil feedstocks: case studies of genetic modifications to improve very long-chain fatty acid and oil content in seeds", Biofuels, Bioproducts and Biorefining 4(5), 2010, pp. 538-561.

Tripathi, M. K. et al., "Glucosinolates in animal nutrition: A review", Animal Feed Science and Technology 132(1-2), 2007, pp. 1-27.

Warwick, SI et al., "Guide to Wild Germplasm of *Brassica* and Allied Crops (tribe Brassiceae, Brassicaceae)", 3rd Edition, Part III, Interspecific and intergeneric hybridization data, 2009, https: / /brassica.infolinfo /publications/luidewild/ Guide_ed.3_Introd_16July2009.pdf, accessed Nov. 20, 2014.

Kin, Hangshu et al., "Mid-Infrared Spectral Characteristics of Lipid Molecular Structures in *Brassica carinata* Seeds: Relationship to Oil Content, Fatty Acid and Glucosinolate Profiles, Polyphenols, and Condensed Tannins", Journal of Agricultural and Food Chemistry 62(32), 2014, pp. 7977-7988.

Huang, et al., "Extrusion processing of rapeseed meal for reducing glucosinolates", Animal Feed Science Technology 56 (1995) pp. 1-9.

Yuan, Deyum. "Analysis of oilseed glucosinolates and their fate during pressing or dehulling". Jun. 2014. (Year: 2014).

COPA, 2016, Trading Rules for the North American Sales of Bulk/Pelletized Canola Meal, Rule 1-Quality, Canadian Oilseed Processors Association.

EFSA, 2008, Glucosinolates as Undesirable Substances in Animal Feed, The EFSA Journal 590: 1-76.

Safety Data Sheet 2014, Global Safety Management, Inc.

Bhandari et al (2015) "Comparison of Glucosinolate Profiles in Different Tissues of Nine *Brassica* Crops", Molecules 20:15827-15841.

Daxenbichler, M. E., et al. (1991). "Glucosinolate composition of seeds from 297 species of wild plants." Phytochemistry 30(8): 2623-2638.

Sharafi et al., 2015, Oil Content and Fatty Acid Composition in *Brassica* Species, International Journal of Food Properties, 18:10, 2145-2154.

Extended European Search Report dated Dec. 17, 2020 for European Patent Application No. 20180016.6.

* cited by examiner

METHOD FOR REMOVING GLUCOSINOLATES FROM OILSEED MEALS

CROSS REFERENCE TO RELATED APPLICATIONS

This application is a continuation of U.S. Ser. No. 15/558,153, filed on Sep. 13, 2017, which is a U.S. National Phase Application under 35 U.S.C. 371 of International Application No. PCT/CA2016/051401 filed on Nov. 29, 2016 and published in English as WO 2017/091891 A1 on Jun. 8, 2017. This application is based on and claims the benefit of priority from U.S. Provisional Patent Application No. 62/262,032 filed Dec. 2, 2015. The entire disclosures of all of the above applications are incorporated herein by reference.

FIELD

The present application relates to methods of removing glucosinolates from oilseed meals.

BACKGROUND

*Brassica carinata* is a member of the Brassicaceae (formerly Cruciferae) family, commonly known as the mustard family. The genus *Brassica* is a member of the tribe Brassiceae in the mustard family (Warwick et al. 2009). In addition to *B. carinata*, the *Brassica* genus includes several economically important oilseed crop species: *B. juncea* (L). Czern. (brown mustard), *B. napus* L. (rape, Argentine canola), *B. nigra* (L.) W. D. J. Koch (black mustard), and *B. rapa* L. (field mustard, Polish canola). The genus Brassica also includes *B. oleracea* L. food crops, including cabbage, broccoli, cauliflower, Brussels sprouts, kohlrabi and kale. The six Brassica species are closely related genetically, as described in the Triangle of U (Nagaharu, 1935, reviewed in Branca and Cartea, 2011). *Brassica carinata* is an amphidiploid (BBCC, 2n=34) thought to be derived from inter-specific hybridization of the diploid species *B. nigra* L. (BB, 2n=16) and *B. oleracea* L. (CC, 2n=18; Prakash et al., 2012).

Recent breeding efforts have focused on the development of new oilseed feedstock crop for biofuels (e.g. ethanol, biodiesel, bio-jet fuel), bio-industrial uses (e.g., bio-plastics, lubricants) and specialty fatty acids (e.g., erucic acid); Taylor et al., 2010. Chief among these are members of the Brassicaceae family: *Brassica carinata* (Ethiopian mustard), *Camelina sativa* (False flax), *Thlaspi arvense* (pennycress) and *Crambe abyssinica* (Crambe). These species have been selected not only because of their potential for providing a high quality feedstock oil but also because of their ability to be grown sustainably in many regions of North America and elsewhere with minimal need for land use change nor displacement of other crops grown for food (Drenth et al., 2014, 2015).

*Brassica carinata* was assessed in the mid-1980s as a potential alternative oilseed crop for North America (Getinet, 1986; Getinet et al., 1996). In Spain and Italy, *Brassica carinata* seed oil is used for biofuel (Bouaid et al., 2005; Cardone et al., 2002, 2003; Gasol et al., 2007, 2009) and as a bio-industrial feedstock with many uses (e.g. in lubricants, paints, cosmetics, plastics). In Canada and the US, *Brassica carinata* is also being exploited as a biofuel feedstock (Blackshaw et al., 2011; Taylor et al., 2010; Marillia et al., 2014; Drenth et al., 2014, 2015), and oil extracted from Brassica carinata seed has been used for the production of green bio-diesel and bio-jet fuel. In October 2012, experimental aviation flights by the National Research Council of Canada using the world's first 100% bio-jet fuel were successful (National Research Council of Canada 2013).

While the oils produced by *Brassica carinata* and other novel oilseed crops are of great value largely because of their utility as an industrial feedstock, the meal produced as part of the oil extraction process is a potentially valuable co-product in its own right. For example, the protein rich and low fiber meal can be used as an additive in livestock and poultry feed rations. Its only limitation as a feed additive is its relatively high content of anti-nutritional compounds, chiefly glucosinolate.

Glucosinolates constitute a large family of over 100 related molecules with a common sulfur containing core structure and with side chains of varying size and chemistry (Fahey et al., 2001; Halkier and Gershenzon, 2006). While glucosinolates are found in many plant structures (leaf, vascular tissue, stem, root, and flowers, to cite some examples), they are accumulated in high concentrations in the seed (Bellostas et al., 2004). This is particularly true for the oil seed brassicas. These compounds and their metabolites can impact the taste of the meal, reducing its palatability and in some cases (dependant on the type of glucosinolate and glucosinolate metabolites present) can also adversely impact the animal's health directly. For example, hydrolysis products of beta hydroxyalkenyl glucosinolates have been shown to possess goitrogenic activity in animal models (reviewed in Fahey et al., 2001). This is particularly an issue in monogastric animals such as swine, but poultry and cattle can be susceptible to varying degrees. Thus glucosinolate reduction in oil seed meal is an important and desirable objective and can have significant benefits in terms of meal value.

Current commercial varieties of *Brassica carinata* seed contain appreciable levels of glucosinolate (60-100 µmol/g). The predominant glucosinolate species in *Brassica carinata* seed is sinigrin (2-propenylglucosinolate, also known as allyl glucosinolate) comprising more than 90% of the total glucosinolate content. This is quite distinct from other commercial brassica oilseeds such as canola type *Brassica napus*, which although lower in overall seed glucosinolate levels (5-12 µmol/g) than *Brassica carinata*, has a very different chemical profile, with progoiterin (2-(R)-2-Hydroxy-3-butenylglucosinolate), gluconapin (3-Butenylglucosinolate) and 4 hydroxyglucobrassicin (4 hydroxyindole methylglucosinolate) being the predominant species and with little or no sinigrin (Xin et al., 2014). Due to the relatively high levels of glucosinolate in the seed of *Brassica carinata*, carinata meal usage as a feed additive is currently limited to cattle and other ruminant species that are relatively tolerant of glucosinolate. Even in this case however, the amounts of carinata meal that can be included are limited to 10 percent due to the glucosinolate levels. The amounts of camelina meal that can be included in beef cattle feed rations are similarly limited.

Several approaches have been taken to achieve reduction in glucosinolate levels in oilseeds. One group of approaches involves processing methods to physically or chemically remove glucosinolates during the processing of the oilseed into its end products while the other involves manipulation of the oilseed varieties through breeding and selection to produce varieties that accumulate much lower levels of glucosinolate within the seed itself. The latter approach has largely supplanted the first since, over a number of years, low glucosinolate varieties have been successfully obtained in many brassica oilseed species, including *B. napus*, *B. rapa* and *B. juncea*. Thus, the requirement for reduction of glucosinolate levels by processing has largely been rendered superfluous for specific varieties within these species, but for many other Brassicaceae species, processing to reduce glucosinolate levels remains a viable option. To date there has been no description on how such processes can be used to reduce glucosinolate content of *Brassica carinata* meal. In particular, the art does not describe the processes and temperatures that could be applied to *Brassica carinata* seed that is subject to oil extraction using solvent to produce a low glucosinolate meal product. It is an object of the present invention to provide a novel method for obtaining *Brassica carinata* solvent extracted meal with reduced glucosinolates.

Processing methodologies to reduce glucosinolates can be divided into two general classes, those that focus on the direct removal of glucosinolate and those that rely on conversion of the glucosinolate to a metabolic byproduct, isothiocyanate, and then subsequent physical removal of the isothiocyanate. Before considering these two broad classes of removal processes in greater detail. It would be instructive to review the current state of the art in oilseed processing at industrial scale.

Processing of brassica oilseeds to extract the oil involves multiple steps. Typically the seeds are cleaned then crushed in a roller mill to generate flakes of 0.3-0.38 mm in thickness. The flaked seed then undergoes a process known as cooking whereby it is conveyed to a heated drum where the flakes are cooked at elevated temperatures (typically from 70-90° C.) for up to 20 min. The cooking helps to reduce the viscosity of the oil to allow for more efficient extraction in subsequent steps, but it also inactivates the endogenous myrosinase enzyme. Cooked seed flakes are then pressed in a series of screw presses or expellers which can remove 50-60% of the oil. Aside from the oil which is removed for further processing, the pressing produces a meal cake that is ideal for solvent extraction. Using several cycles of countercurrent extraction, the meal cake is treated with hexane to remove the residual oil from the meal. The meal is then transferred to a desolventizer-toaster where it is heated to remove remaining hexane; the final step of the process, called toasting, involves injection of steam into the meal to remove the last traces of hexane. The meal is then cooled and dried by blowing forced air through it.

In some cases, the seed can also be processed using a cold press methodology which is similar to above except it does not involve the use of hexane to remove residual oil from the oil cake, resulting in a meal with much higher oil composition.

When canola seed is crushed to yield oil and meal, seed glucosinolate reduction is not a preeminent consideration in the design of the process. All steps involving heating, i.e. the cooking step as well as the desolventizing, toasting step, are designed to require the lowest heat required to achieve their respective ends. This is to achieve the best balance of oil yield and meal quality, the latter being most sensitive to the deleterious effect of high heat on protein levels and quality. When the seed to be processed is not canola quality, however, consideration must be given to means of reducing the endogenous glucosinolates to allow for improved meal and oil quality. As glucosinolates are to some extent heat labile, the cooking step can be employed for glucosinolate removal. Increasing the cooking temperature to as high as 120° C. has been employed to reduce glucosinolate levels; however, this can have deleterious effects on heat labile proteins of the meal, reducing its value substantially. Other modifications of the crushing process have been described with the goal of reducing glucosinolate in meal. The use of an extruder apparatus, used instead of the typical screw process, has been shown to be beneficial in reduction of glucosinolates from rapeseed meal. However, these processes have not been previously described for *Brassica carinata*.

There are many examples in the literature of processes to reduce glucosinolate from meal that has already been processed for removal of oil, i.e. that had previously gone through a process similar to that described in the previous paragraphs. The earliest attempts at direct reduction of glucosinolates involved application of heat or heat combined with methods to reduce the particle size of the meal (i.e. micronization and extrusion technologies). Heating in the form of microwave exposure was shown to reduce glucosinolate levels via degradation (Aumaitre et al., 1989). The authors estimated that microwave heating methodologies can result in up to 25% reduction in glucosinolate levels. Application of heating, micronization and treatment in an extruder were each shown to be useful for glucosinolate reduction and the magnitude of the reduction was increased if chemical agents such as alkali or ammonium were added to the meal (Fenwick et al., 1986). However, the authors of this study noted that the magnitude of glucosinolate reduction was greatest under conditions which also affected the integrity of other nutritional components. For example, application of excessive heat (however applied) while significantly reducing glucosinolate levels, also hastened degradation of proteins via the Maillard reaction (Anderson-Haferman et al., 1993). Such unwanted effects on protein quality are a particular property of this class of glucosinolate reduction strategies. It would also in many cases necessitate investment in new equipment and additional processing steps, which would affect the cost of processing and ultimately of the meal itself. As above, the art is void of such approaches with *Brassica carinata*.

Processes have been developed to remove glucosinolates from meal based on their interactions with aqueous solvents (reviewed by Tripathi and Mishra, 2007). Significant loss of glucosinolates due to hydrolysis can occur during prolonged soaking in water. Supplementation of soaking buffer with metal ions (such as Cu++) could further potentiate the removal of glucosinolates. While the process is economical, losses of dry matter during the soaking can affect the quality of and quantity of meal for feed applications.

It was recognized quite early that under the right conditions glucosinolate content of the meal could be converted to isothiocyanate almost quantitatively by action of myrosinase, which could subsequently be removed by a variety of methods. In fact the action of myrosinase on glucosinolate is tightly controlled during the seed crushing process. Normally sequestered within the cellular structure, myrosinase is mobilized by processes which physically disrupt the seed's structure and integrity, such as crushing. This mobilization brings it into contact with the glucosinolate of the meal fraction and under the appropriate conditions of temperature, pH and humidity could quantitatively convert the glucosinolate to isothiocyanate. While this would be beneficial as regards meal quality it would have other less desirable consequences. For example, the isothiocyanate, being very lipid soluble could potentially adulterate the oil component, and result in an unacceptably high oil sulphur content.

In addition, myrosinase catalyzes the conversion of sinigrin (allyl glucosinolate) to allyl isothiocyanate. Allyl isothiocyanate is volatile (Dai and Lim, 2014) and is also known as volatile oil of mustard. Allyl isothiocyanate is highly pungent, and is responsible for the pungent taste of horse radish and wasabi root. In pure form it can be toxic, acting as an irritant to skin and mucous membranes. Isothiocyanates also impart a pungent taste to a feed ration, which reduces its palatability and adversely affects the livestock's intake of the meal.

For these reasons, the oilseed crushing process described earlier incorporates the heating step before crushing in part to inactivate the myrosinase, ensuring that the conversion of glucosinolates to isothiocyanates does not take place.

Nevertheless, others have described processes whereby myrosinase could be used to advantage to convert glucosinolate to isothiocyanate at later stages of the crushing process (i.e. after the removal of the oil has been completed). In this scenario, an exogenous source of myrosinase is added back to the processed meal and allowed to react with the endogenous glucosinolate under optimized conditions. The released isothiocyanate could be then extracted from the meal using a variety of different solvents (see U.S. Pat. No. 4,244,973). Much like the direct glucosinolate removal processes, the utility of this approach is greatly influenced by the additional costs and equipment required to process the meal and the potential deleterious effects of the solvent treatment on meal quality.

With a new generation of oilseed crops being developed to provide oil based feedstock for industrial purposes, the economic value of these crops can be greatly enhanced if other value added by-products of the oil extraction process can be commercially exploited. *Brassica carinata*, for example, produces a seed oil that is highly valued as an industrial feedstock while its meal rivals soybean meal in terms of protein quality and low fiber content. If the levels of glucosinolate in carinata meal could be reduced to those of double zero canola quality meal, it would significantly increase the market value for carinata meal as a feed additive. While efforts to develop low glucosinolate varieties of carinata are ongoing, there exists a need to develop an economical and effective process to reduce the glucosinolate levels of existing sources of carinata meal. The process should be easily adaptable to existing oil crushing plants in terms of cost, time and equipment so as not to constitute a deterrent to its adoption by the industry. Moreover, the process should be sufficiently gentle so as not to compromise the advantage that carinata holds in terms of protein content over other oilseed meals. Such a process could also be adapted to other oilseeds by virtue of their common characteristics. In this regard, it is instructive to note that even the best current varieties of canola have small but measurable quantities of glucosinolates remaining in their meal and that the ability to remove these in a cost effective way may enable new products and new markets for canola meal as well.

While the current art teaches how glucosinolate levels can be reduced in oilseed meals, the methods of reduction invariably involve processes that that can adversely affect the integrity of the meal protein constituents either through denaturation or via extractive losses. As protein constitutes the most important nutritional component of meal, processes that affect the protein content or quality can also affect the value of the meal.

SUMMARY

In one embodiment, the present invention provides a process for removing at least one glucosinolate from a meal fraction of oilseed comprising: (a) treating the meal fraction of oilseed with exogenous myrosinase to convert the at least one glucosinolate to a volatile isothiocyanate; and (b) removing the volatile isothiocyanate from the treated meal fraction of oilseed under conditions of mild heat and negative pressure.

In another embodiment, the present invention provides the process described herein for removing at least one glucosinolate from a meal fraction of oilseed, wherein step (a) and step (b) occur simultaneously or sequentially.

In another embodiment, the present invention provides the process described herein for removing at least one glucosinolate from a meal fraction of oilseed, wherein the time for step (a) and step (b) is greater than 2 min, 5 min, 10 min, 15 min, 20 min, 30 min, 1 h, 2 h, 3 h, or 4 h, and less than 9 h, 10 h, 11 h, or 12 h.

In another embodiment, the present invention provides the process described herein for removing at least one glucosinolate from a meal fraction of oilseed, wherein the process further comprises regulating the temperature during step (a) and step (b) to prevent the temperature from exceeding 45° C., 50° C., 55° C., 60° C., 65° C., or 70° C.

In another embodiment, the present invention provides the process described herein for removing at least one glucosinolate from a meal fraction of oilseed, wherein the process further comprises carrying out step (a) and step (b) in a reaction vessel under negative pressure of over 10%, 20%, 30%, 40%, 50%, 60%, 70%, 80%, 90%, 95%, 98%, or 99% vacuum and evacuating volatile substances from the reaction vessel.

In another embodiment, the present invention provides the process described herein for removing at least one glucosinolate from a meal fraction of oilseed, wherein the process further comprises increasing the temperature to over 60° C., 65° C., 70° C., 75° C., 80° C., 85° C., or 90° C., but to less than 95° C., 100° C., 105° C., 110° C., or 115° C., following step (a) and step (b) and further incubating the meal fraction of oilseed until the moisture content of the meal fraction of oilseed decreases to less than 20%, 18%, 16%, 14%, 12%, or 10%.

In another embodiment, the present invention provides the process described herein for removing at least one glucosinolate from a meal fraction of oilseed, wherein the process further comprises increasing the temperature to over 60° C., 65° C., 70° C., 75° C., 80° C., 85° C., or 90° C., but to less than 95° C., 100° C., 105° C., 110° C., or 115° C., following step (a) and step (b) and further incubating the meal fraction of oilseed until the moisture content of the meal fraction of oilseed decreases to less than 20%, 18%, 16%, 14%, 12%, or 10%, and wherein the process further comprises carrying out the further incubation in a reaction vessel under negative pressure of over 10%, 20%, 30%, 40%, 50%, 60%, 70%, 80%, 90%, 95%, 98%, or 99% vacuum and evacuating volatile substances from the reaction vessel.

In another embodiment, the present invention provides the process described herein for removing at least one glucosinolate from a meal fraction of oilseed, wherein the process further comprises continuously mixing the meal fraction of oilseed and exogenous myrosinase.

In another embodiment, the present invention provides the process described herein for removing at least one glucosinolate from a meal fraction of oilseed, wherein the process further comprises preheating the meal fraction of oilseed to between 25° C. to 40° C. prior to step (a).

In another embodiment, the present invention provides the process described herein for removing at least one glucosinolate from a meal fraction of oilseed, wherein the process further comprises providing the exogenous myrosinase in the form of a triggering solution comprising a slurry of defatted meal in water.

In another embodiment, the present invention provides the process described herein for removing at least one glucosinolate from a meal fraction of oilseed, wherein the process further comprises providing the exogenous myrosinase in the form of a triggering solution comprising a slurry of defatted meal in water, and wherein the defatted meal is from oilseed of a plant species of the Brassicaceae family.

In another embodiment, the present invention provides the process described herein for removing at least one glucosinolate from a meal fraction of oilseed, wherein the process further comprises providing the exogenous myrosinase in the form of a triggering solution comprising a slurry of defatted meal in water, and wherein the defatted meal is from oilseed of *Sinapis alba* or *Brassica carinata*.

In another embodiment, the present invention provides the process described herein for removing at least one glucosinolate from a meal fraction of oilseed, wherein the process further comprises providing the exogenous myrosinase in the form of a triggering solution comprising a slurry of defatted meal in water, and wherein the triggering solution further comprises ascorbic acid.

In another embodiment, the present invention provides the process described herein for removing at least one glucosinolate from a meal fraction of oilseed, wherein the process further comprises adding triggering solution to the meal fraction of oilseed in a ratio of 0.5:1, 0.55:1, 0.6:1, 0.65:1, or 0.7:1 (w/w) triggering solution: meal fraction of oilseed.

In another embodiment, the present invention provides the process described herein for removing at least one glucosinolate from a meal fraction of oilseed, wherein the meal fraction of oilseed results from hexane extraction of oilseeds.

In another embodiment, the present invention provides the process described herein for removing at least one glucosinolate from a meal fraction of oilseed, wherein the meal fraction of oilseed results from hexane extraction of oilseeds, wherein the hexane extraction was carried out on flaked and cooked oilseed, and wherein the cooking was carried out at a temperature greater than 70° C., 75° C., 80° C., 85° C., 90° C., 95° C., 100° C., 105° C., 110° C., 115° C., 120° C., 125° C., 130° C., 135° C., or 140° C., but less than 150° C., 155° C., 160° C., 165° C., 170° C., 175° C., or 180° C.

In another embodiment, the present invention provides the process described herein for removing at least one glucosinolate from a meal fraction of oilseed, wherein the meal fraction of oilseed results from hexane extraction of oilseeds, wherein the hexane extraction was carried out on flaked and cooked oilseed, and wherein the duration of cooking was at least 10, 12, 14, 15, 16, 17, 18, 19, 20, 22, 24, 26, 28 or 30 minutes, but less than 60, 70, 80, 90, or 100 minutes.

In another embodiment, the present invention provides the process described herein for removing at least one glucosinolate from a meal fraction of oilseed, wherein the meal fraction of oilseed results from hexane extraction of oilseeds, and wherein the hexane extraction was carried out on flaked and cooked oilseed that had been pressed using an expeller or a screw press.

In another embodiment, the present invention provides the process described herein for removing at least one glucosinolate from a meal fraction of oilseed, wherein the meal fraction of oilseed results from hexane extraction of oilseeds, wherein the hexane extraction was carried out on flaked and cooked oilseed, and wherein the resultant meal cake underwent treatment in a desolventizer-toaster at a temperature of at least 50° C., 55° C., 60° C., 65° C., 70° C., 75° C., 80° C., 85° C., 90° C., 95° C., 100° C., 105° C., 110° C., 115° C., 120° C., 125° C., or 130° C., but less than 135° C., 140° C., 145° C., or 150° C.

In another embodiment, the present invention provides the process described herein for removing at least one glucosinolate from a meal fraction of oilseed, wherein the reaction vessel is a desolventizer-toaster, and wherein step (a), step (b), and the further incubation are part of a desolventizer-toaster step of hexane extraction of oilseeds.

In another embodiment, the present invention provides the process described herein for removing at least one glucosinolate from a meal fraction of oilseed, wherein the meal fraction of oilseed results from cold press processing of oilseeds.

In another embodiment, the present invention provides the process described herein for removing at least one glucosinolate from a meal fraction of oilseed, wherein the meal fraction of oilseed to be treated is pelleted and homogenized by hammer-milling to a size of less than 5.66 mm, 4.75 mm, 4.00 mm, 3.36 mm, 2.83 mm or 2.38 mm.

In another embodiment, the present invention provides the process described herein for removing at least one glucosinolate from a meal fraction of oilseed, wherein the meal fraction of oilseed is from oilseed of a plant species of the family Brassicaceae.

In another embodiment, the present invention provides the process described herein for removing at least one glucosinolate from a meal fraction of oilseed, wherein the meal fraction of oilseed is from oilseed of *Brassica juncea, Brassica napus, Brassica rapa, Brassica carinata, Brassica nigra, Cammelina sativa, Crambe abyssinica*, or *Thlaspi arvense*.

In another embodiment, the present invention provides a process for removing at least one glucosinolate from a meal fraction of a *Brassica carinata* oilseed comprising heating and applying pressure to the oilseed before, during, or after the extraction of oil.

In another embodiment, the present invention provides the process described herein for removing at least one glucosinolate from a meal fraction of a *Brassica carinata* oilseed comprising heating and applying pressure to the oilseed before, during, or after the extraction of oil, wherein the temperature during heating is greater than 70° C., 75° C., 80° C., 85° C., 90° C., 95° C., 100° C., 105° C., 110° C., 115° C., 120° C., 125° C., 130° C., 135° C., or 140° C., but less than 150° C., 155° C., 160° C., 165° C., 170° C., 175° C., or 180° C.

In another embodiment, the present invention provides the process described herein for removing at least one glucosinolate from a meal fraction of a *Brassica carinata* oilseed comprising heating and applying pressure to the oilseed before, during, or after the extraction of oil, wherein the duration of heating is at least 10, 12, 14, 15, 16, 17, 18, 19, 20, 22, 24, 26, 28, or 30 minutes, but less than 60, 70, 80, 90, or 100 minutes.

In another embodiment, the present invention provides the process described herein for removing at least one glucosinolate from a meal fraction of a *Brassica carinata* oilseed comprising heating and applying pressure to the oilseed before, during, or after the extraction of oil, wherein the process further comprises applying the pressure using an expeller or a screw press.

In another embodiment, the present invention provides a process for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the temperature of heating in step (a) is greater than 70° C., 75° C., 80° C., 85° C., 90° C., 95° C., 100° C., 105° C., 110° C., 115° C., 120° C., 125° C., 130° C., 135° C., or 140° C., but less than 150° C., 155° C., 160° C., 165° C., 170° C., 175° C., or 180° C.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the duration of heating in step (a) is at least 10, 12, 14, 15, 16, 17, 18, 19, 20, 22, 24, 26, 28, or 30 minutes, but less than 60, 70, 80, 90, or 100 minutes.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process further comprises applying the pressure in step (a) using an expeller or a screw press.

BRIEF DESCRIPTION OF THE FIGURES

In the figures, which illustrate embodiments of the invention by way of example only.

DETAILED DESCRIPTION

Figure 1:
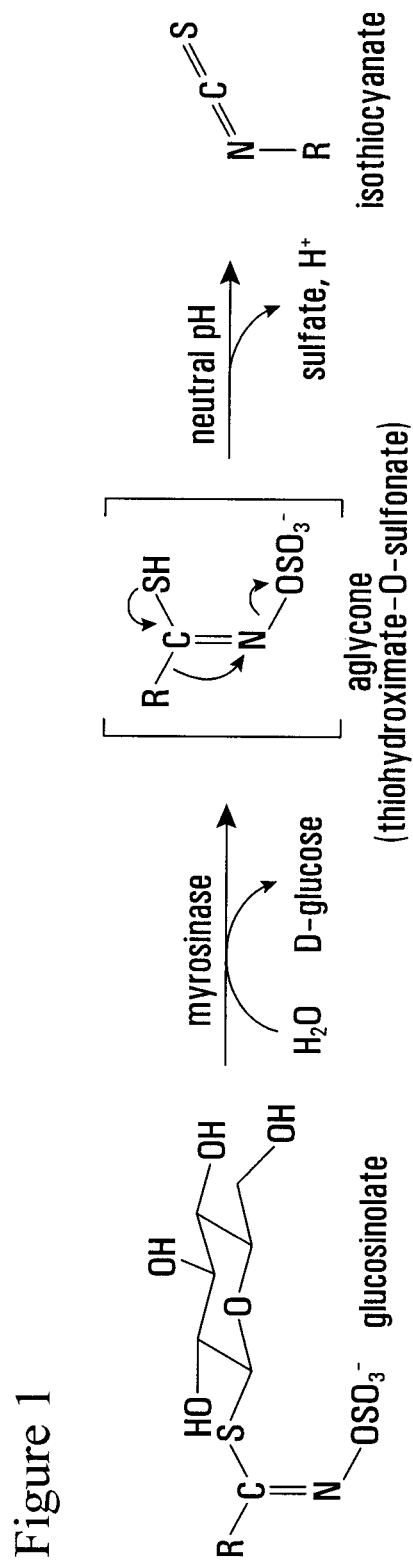
FIG. 1 is diagram of the enzymatic reaction converting glucosinolate to isothiocyanate catalyzed by myrosinase.

With a new generation of oilseed crops, such as *Brassica carinata*, being developed to provide oil based feedstock for industrial purposes, there exists a need to develop an economical and effective process to reduce the glucosinolate levels of the meal in order to be able to commercially exploit the meal, including, for example, as a feed additive for animal feeds.

The process should be easily adaptable to existing oil crushing plants in terms of cost, time and equipment so as not to constitute a deterrent to its adoption by the industry. Moreover the process should be sufficiently gentle so as not to compromise the advantage that carinata holds in terms of protein content over other oilseed meals.

"Animal feeds" are those processed formulations that are fed to livestock, as opposed to those sources of nutrition that animals may forage for themselves. Animal feeds may be formulated to provide optimum nutrition for particular applications, such as maximizing weight gain and meat quality of beef cattle in the feed lot, or maximizing milk production of lactating dairy cattle. For poultry, feeds may be formulated to provide a consistent nutritional source to supplement or even replace the variable nutritional quality obtained through foraging. While the composition of feeds may vary greatly based on animal, application and geography, a constant requirement is the addition of supplements to the base feed to improve its protein content. Typical of such supplements are dried distiller grains, consisting of the spent fermented mash obtained from breweries or spirit distilleries, as well as meal from soybean, canola meal, carinata or mustard, all obtained after seed crush and extraction of the oil fraction.

"Anti-nutritional" is a general description of a number of compounds found in Brassica and other seed meals that reduce the nutritional benefit of animal feed products in which the meal is used as an additive. Glucosinolates and isothiocyanates are classified as anti-nutritionals since, when present in high enough concentrations, they impart a bitter and pungent taste to the feed ration, reducing its palatability and adversely affecting the livestock's intake of the meal.

Glucosinolates

"Glucosinolates" are β-thioglucoside N-hydroxysulfates with a variable side chain (R) and a sulfur-linked β-d-glucopyranose moiety. They represent a large and heterogeneous family of naturally occurring compounds; more than 120 varieties are known to occur in nature (Fahey, et al., 2001). Glucosinolates have the following chemical structure:

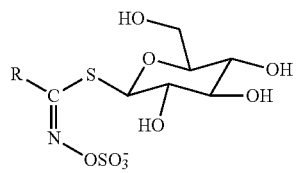

"Sinigrin" is the common name of allyl glucosinolate (or 2-propenyl glucosinolate), where the R position has been substituted with an allyl group. Sinigrin is the predominant glucosinolate species found in *Brassica carinata* and *Brassica nigra* seeds, and is also found, in lesser amounts in seeds of other Brassicaceae species. Sinigrin has the following chemical structure:

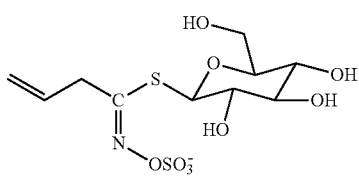

Glucosinolates are found in many species of plants, particularly those within the order *Brassicales*, but also among plants of the genus *Drypetes* and the genus *Putranjiva* (both genera of the *Putranjivaceae* family). They are accumulated to high levels in the seed, as well as other plant tissues. This is particularly true for the oil seed brassicas. The glucosinolates found in meal samples of oilseeds include sinigrin, sinalbin, gluconapin, and gluconasturtin, among others, and their relative proportions can vary significantly depending on the species. These compounds and their metabolites can impact the taste of the meal, reducing its palatability and in some cases (dependant on the type of glucosinolate and glucosinolate metabolites present) can also adversely impact the health of an animal that has consumed plant material containing glucosinolates. Glucosinolate reduction in oil seed meal is an important and desirable objective and can have significant benefits in terms of meal value for animal feed.

Isothiocyanates

"Isothiocyanate" is a chemical group formed by substituting the oxygen in a isocyanate group with a sulfur. Isothiocyanate has the following chemical structure:

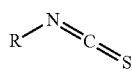

Many natural isothiocyanates from plants are produced by conversion of glucosinolates catalyzed by the enzyme myrosinase. Conversion of sinigrin (allyl glucosinolate) catalyzed by myrosinase yields the product allyl isothiocyanate (also known as volatile oil of mustard). Allyl isothiocyanate is highly pungent and volatile, and is responsible for the pungent taste of horse radish and wasabi root. In pure form it can be toxic, acting as an irritant to skin and mucous membranes. Allyl isothiocyanate has the following chemical structure:

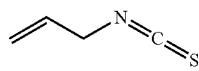

Myrosinase

"Myrosinase", also known as thioglucosidase, is an enzyme that catalyzes the conversion of glucosinolates to isothiocyanate compounds, which are extremely pungent and volatile. FIG. 1 shows the enzymatic reaction. Myrosinase first catalyzes the removal of D-glucose from glucosinolate, which results in an aglycone intermediate in the form of thiohydroximate-O-sulfonate. Myrosinase then further catalyzes the removal of the sulfate group to generate isothiocyanate.

While not the sole source of myrosinase, the seeds and other tissues of plants in the Brassicaceae family are rich in myrosinase. *Sinapis alba* is a particularly rich source of myrosinase. In a study carried out by Atle Bones (Bones, 1990), *Sinapis alba* seed was found to contain 10 times more myrosinase than that of *Brassica napus* or *Brassica rapa*, while earlier work (Henderson and McEwen, 1972) demonstrated that myrosinase activity from crude extracts of *Sinapis alba* seeds greatly exceeded that of other extract sources, including *Brassica Juncea, Brassica nigra, Brassica napus, Brassica rapa* and *Crambe abyssinica*. Other sources of myrosinase may include cresses, horseradish, wasabi, and camelina. However, any plant that expresses myrosinase in appreciable amounts, or organisms that are engineered to express glucosinolate heterologously, such as bacteria, or plant and/or mammalian cell cultures, can potentially be used as a source of myrosinase enzyme of varying degrees of purity.

Myrosinase exists as several forms in *Brassicaceae*, and are encoded by at least three subfamilies of genes, denoted MA, MB, and MC, with the potential for multiple genes in each subfamily. However, in principle, any myrosinase will accept all glucosinolates as substrates (Rask, 2000). Myrosinase is thought to be found exclusively in cells referred to as myrosin cells (reviewed in Kissen et al., 2009). Their relative localization with respect to glucosinolates is less well understood. In some tissues, the enzyme and substrate are thought to be present in the same cells but in different cellular compartments, while in other tissues, they are thought to segregate in different cell populations. Regardless of their relative distributions, it is thought that when the plant tissue is crushed or damaged, the two stores are brought together, bringing myrosinase in contact with glucosinolate and initiating the conversion of the glucosinolate to isothiocyanate. Thus, the myrosinase reaction serves the function of providing plants with a unique chemical defense against predation by herbivores Oilseeds "Oilseed" refers to any crop species where oil is extracted from the seeds of these grains for food or industrial purposes, and includes Brassicaceae oilseeds such as canola, and non-Brassicaceae oilseeds, such as flaxseed, soybean, safflower, and sunflower. An example of a crop species that produces a seed used primarily for the production of edible oil is *Brassica napus*. An example of a crop species that is used primarily in the production of industrial feedstock oil is *Brassica carinata*.

*Brassica carinata* is commonly referred to as Ethiopian Mustard, and is a domesticated oilseed *Brassica* species. *Brassica carinata* is an amphidiploid, meaning it is a stable hybrid between two diploid *Brassica* precursor species, specifically *Brassica nigra* and *Brassica oleracea*. The seed of *Brassica carinata* can contain more than 40% by weight of oil, which can be used as an industrial feedstock as a replacement for petroleum in a number applications.

*Sinapis alba* is commonly referred to as white mustard, and is an annual crop of the Brassicaceae family. The seed of *Sinapis alba*, used in the preparation of condiment mustard, contains high concentrations of glucosinolates, a sulfur containing compound that offers the plant protection from insect predation.

Meal

"Meal" refers to the remaining fraction of the seed content after extraction of the oil, and consists mainly of protein. In the case of *Brassica carinata* this meal fraction is particularly protein rich relative to other *Brassica* oilseed species and has thus been proposed as a potential high value additive in animal feed applications. For the present invention, the meal to be treated can be derived from any process the extracts oil from oilseeds, leaving the meal, including, without limitation hexane extraction and a cold press process.

Hexane Extraction to Extract the Oil from Oilseeds

Hexane extraction typically occurs by the following process. First, the oilseeds are prepared for the hexane extraction. The oilseeds are cleaned, and then crushed in a roller mill to generate flakes of 0.3-0.38 mm in thickness. The flaked seed is then conveyed to a heated drum where the flakes are cooked at elevated temperatures (from 80-150° C., depending on the source of the seed) for up to 20 min. Cooked seed flakes are then pressed in a series of screw presses or expellers which can remove 50-60% of the oil. Aside from the oil which is removed for further processing, the pressing produces a meal cake that is ideal for solvent extraction.

"Meal cake" refers to the state of the seed meal after it has gone through the flaking and cooking stage and has been mechanically pressed to extrude the bulk of the oil. The term refers to the physical character of the meal at this stage, which has been compressed into a cake-like mass rich in protein and still containing appreciable residual oil.

Next, using several cycles of countercurrent extraction, the meal cake is treated with hexane to remove the residual oil from the meal. After the oil has been removed from the flakes or meal cake, the meal will contain approximately 30% of solvent (hexane) content.

"Defatted meal" refers to the state of the meal after the meal cake has been solvent extracted to remove the last traces of residual oil.

Typically, the meal would then undergo toasting and desolventizing to remove the hexane solvent and reduce the moisture content to 12% or less. The meal is transferred to a desolventizer-toaster, where it is heated to remove remaining hexane. Most of the solvent is removed by heating the meal on steam-heated plates. Removal of the final traces of solvent is carried out by injecting steam through the meal (the actual toasting process).

In the course of the toasting process (roughly 30 minutes in duration), the meal is exposed to temperatures ranging from 95-115° C. and moisture increases to 12-18%. Subsequently, the meal is cooled and dried via forced air circulation until a final moisture content of 12% or less is achieved. The meal is then pelletized or granulated depending on the requirements of the end user.

Cold Press Processing

In some cases the seed can also be processed using a cold press methodology, which is similar to above except it does not involve the use of hexane to remove residual oil from the oil cake, resulting in a meal with much higher oil composition.

Process to Remove Glucosinolates from the Meal Fraction of Oilseeds

In one embodiment, the invention described herein provides a process for removing at least one glucosinolate from a meal fraction of oilseed comprising: (a) treating the meal fraction of oilseed with exogenous myrosinase to convert the at least one glucosinolate to a volatile isothiocyanate; and (b) removing the volatile isothiocyanate from the treated meal fraction of oilseed under conditions of mild heat and negative pressure.

In another embodiment, the invention provides the process described herein for removing at least one glucosinolate from a meal fraction of oilseed, wherein step (a) and step (b) occur simultaneously.

In another embodiment, the invention provides the process described herein for removing at least one glucosinolate from a meal fraction of oilseed, wherein step (a) and step (b) occur sequentially.

In another embodiment, the invention provides the process described herein for removing at least one glucosinolate from a meal fraction of oilseed, wherein the total time for step (a) and step (b) is greater than 2 min, 5 min, 10 min, 15 min, 20 min, 30 min, 1 h, 2 h, 3 h, or 4 h, and less than 9 h, 10 h, 11 h, or 12 h.

In another embodiment, the invention provides the process described herein for removing at least one glucosinolate from a meal fraction of oilseed, wherein the total time for step (a) and step (b) is 3 h.

In another embodiment, the processes described herein further comprise the treatment of a seed meal cake containing glucosinolate wherein the treatment involves incubating the meal with an exogenous source of myrosinase, and wherein the hydrolysis product is substantially removed from the seed meal cake by virtue of its high volatility.

Mild Heat

"Mild heat" means a temperature above 0° C., but less than a temperature that would have an adverse effect on protein quality in the meal because of heat denaturation. For example, mild heat can be greater than 25° C. but less than 90° C.

In one embodiment, the invention provides the process described herein for removing at least one glucosinolate from a meal fraction of oilseed, wherein the process further comprises regulating the temperature during step (a) and step (b) to prevent the temperature from exceeding 45° C., 50° C., 55° C., 60° C., 65° C., or 70° C.

In another embodiment, the invention provides the process described herein for removing at least one glucosinolate from a meal fraction of oilseed, wherein the process further comprises regulating the temperature during step (a) and step (b) to prevent the temperature from exceeding 50° C.

In another embodiment, the invention provides the process described herein for removing at least one glucosinolate from a meal fraction of oilseed, wherein the process further comprises regulating the temperature during step (a) and step (b) to prevent the temperature from exceeding 60° C.

Negative Pressure

"Negative Pressure" means any percentage of vacuum. For example, negative pressure can be anything from 0.0001% vacuum to 100% vacuum.

In one embodiment, the invention provides the process described herein for removing at least one glucosinolate from a meal fraction of oilseed, wherein the process further comprises carrying out step (a) and step (b) in a reaction vessel under negative pressure and evacuating volatile substances from the reaction vessel.

In another embodiment, the invention provides the process described herein for removing at least one glucosinolate from a meal fraction of oilseed, wherein the process further comprises carrying out step (a) and step (b) in a reaction vessel under negative pressure of over 10%, 20%, 30%, 40%, 50%, 60%, 70%, 80%, 90%, 95%, 98%, or 99% vacuum and evacuating volatile substances from the reaction vessel.

Post-Treatment Incubation

Following the initial steps of treating the meal fraction of oilseed with exogenous myrosinase to convert the at least one glucosinolate to a volatile isothiocyanate, and removing the volatile isothiocyanate from the treated meal fraction of oilseed under conditions of mild heat and negative pressure, the meal fraction of oilseed can be further heated to dry the meal and to remove additional volatile isothiocyanates.

In one embodiment, the invention provides the process described herein for removing at least one glucosinolate from a meal fraction of oilseed, wherein the process further comprises increasing the temperature to a temperature higher than that of step (b) following step (a) and step (b) and further incubating the meal fraction of oilseed until the moisture content of the meal fraction of oilseed decreases to the required percentage.

In another embodiment, the invention provides the process described herein for removing at least one glucosinolate from a meal fraction of oilseed, wherein the process further comprises increasing the temperature to over 60° C., 65° C., 70° C., 75° C., 80° C., 85° C., or 90° C., but to less than 95° C., 100° C., 105° C., 110° C., or 115° C., following step (a) and step (b) and further incubating the meal fraction of oilseed until the moisture content of the meal fraction of oilseed decreases to less than 20%, 18%, 16%, 14%, 12%, or 10%.

In another embodiment, the invention provides the process described herein for removing at least one glucosinolate from a meal fraction of oilseed, wherein the process further comprises increasing the temperature to 70° C. following step (a) and step (b) and further incubating the meal fraction of oilseed until the moisture content of the meal fraction of oilseed decreases to less than 20%, 18%, 16%, 14%, 12%, or 10%.

In another embodiment, the invention provides the process described herein for removing at least one glucosinolate from a meal fraction of oilseed, wherein the process further comprises increasing the temperature to over 60° C., 65° C., 70° C., 75° C., 80° C., 85° C., or 90° C., but to less than 95° C., 100° C., 105° C., 110° C., or 115° C., following step (a) and step (b) and further incubating the meal fraction of oilseed until the moisture content of the meal fraction of oilseed decreases to less than 12%.

In another embodiment, the invention provides the process described herein for removing at least one glucosinolate from a meal fraction of oilseed, wherein the process further comprises increasing the temperature to 70° C. following step (a) and step (b) and further incubating the meal fraction of oilseed until the moisture content of the meal fraction of oilseed decreases to less than 12%.

In another embodiment, the invention provides the process described herein for removing at least one glucosinolate from a meal fraction of oilseed, wherein the process further comprises increasing the temperature to over 60° C., 65° C., 70° C., 75° C., 80° C., 85° C., or 90° C., but to less than 95° C., 100° C., 105° C., 110° C., or 115° C., following step (a) and step (b) and further incubating the meal fraction of oilseed until the moisture content of the meal fraction of oilseed decreases to less than 20%, 18%, 16%, 14%, 12%, or 10%, and wherein the process further comprises carrying out the post-treatment incubation in a reaction vessel under negative pressure and evacuating volatile substances from the reaction vessel.

In another embodiment, the invention provides the process described herein for removing at least one glucosinolate from a meal fraction of oilseed, wherein the process further comprises increasing the temperature to 70° C. following step (a) and step (b) and further incubating the meal fraction of oilseed until the moisture content of the meal fraction of oilseed decreases to less than 20%, 18%, 16%, 14%, 12%, or 10%, and wherein the process further comprises carrying out the post-treatment incubation in a reaction vessel under negative pressure and evacuating volatile substances from the reaction vessel.

In another embodiment, the invention provides the process described herein for removing at least one glucosinolate from a meal fraction of oilseed, wherein the process further comprises increasing the temperature to over 60° C., 65° C., 70° C., 75° C., 80° C., 85° C., or 90° C., but to less than 95° C., 100° C., 105° C., 110° C., or 115° C., following step (a) and step (b) and further incubating the meal fraction of oilseed until the moisture content of the meal fraction of oilseed decreases to less than 12%, and wherein the process further comprises carrying out the post-treatment incubation in a reaction vessel under negative pressure and evacuating volatile substances from the reaction vessel.

In another embodiment, the invention provides the process described herein for removing at least one glucosinolate from a meal fraction of oilseed, wherein the process further comprises increasing the temperature to 70° C. following step (a) and step (b) and further incubating the meal fraction of oilseed until the moisture content of the meal fraction of oilseed decreases to less than 12%, and wherein the process further comprises carrying out the post-treatment incubation in a reaction vessel under negative pressure and evacuating volatile substances from the reaction vessel.

In another embodiment, the invention provides the process described herein for removing at least one glucosinolate from a meal fraction of oilseed, wherein the process further comprises increasing the temperature to over 60° C., 65° C., 70° C., 75° C., 80° C., 85° C., or 90° C., but to less than 95° C., 100° C., 105° C., 110° C., or 115° C., following step (a) and step (b) and further incubating the meal fraction of oilseed until the moisture content of the meal fraction of oilseed decreases to less than 20%, 18%, 16%, 14%, 12%, or 10%, and wherein the process further comprises carrying out the post-treatment incubation in a reaction vessel under negative pressure of over 10%, 20%, 30%, 40%, 50%, 60%, 70%, 80%, 90%, 95%, 98%, or 99% vacuum and evacuating volatile substances from the reaction vessel.

In another embodiment, the invention provides the process described herein for removing at least one glucosinolate from a meal fraction of oilseed, wherein the process further comprises increasing the temperature to 70° C. following step (a) and step (b) and further incubating the meal fraction of oilseed until the moisture content of the meal fraction of oilseed decreases to less than 20%, 18%, 16%, 14%, 12%, or 10%, and wherein the process further comprises carrying out the post-treatment incubation in a reaction vessel under negative pressure of over 10%, 20%, 30%, 40%, 50%, 60%, 70%, 80%, 90%, 95%, 98%, or 99% vacuum and evacuating volatile substances from the reaction vessel.

In another embodiment, the invention provides the process described herein for removing at least one glucosinolate from a meal fraction of oilseed, wherein the process further comprises increasing the temperature to over 60° C., 65° C., 70° C., 75° C., 80° C., 85° C., or 90° C., but to less than 95° C., 100° C., 105° C., 110° C., or 115° C., following step (a) and step (b) and further incubating the meal fraction of oilseed until the moisture content of the meal fraction of oilseed decreases to less than 12%, and wherein the process further comprises carrying out the post-treatment incubation in a reaction vessel under negative pressure of over 10%, 20%, 30%, 40%, 50%, 60%, 70%, 80%, 90%, 95%, 98%, or 99% vacuum and evacuating volatile substances from the reaction vessel.

In another embodiment, the invention provides the process described herein for removing at least one glucosinolate from a meal fraction of oilseed, wherein the process further comprises increasing the temperature to 70° C. following step (a) and step (b) and further incubating the meal fraction of oilseed until the moisture content of the meal fraction of oilseed decreases to less than 12%, and wherein the process further comprises carrying out the post-treatment incubation in a reaction vessel under negative pressure of over 10%, 20%, 30%, 40%, 50%, 60%, 70%, 80%, 90%, 95%, 98%, or 99% vacuum and evacuating volatile substances from the reaction vessel.

Mixing

During the initial steps of treating the meal fraction of oilseed with exogenous myrosinase to convert the at least one glucosinolate to a volatile isothiocyanate, and removing the volatile isothiocyanate from the treated meal fraction of oilseed under conditions of mild heat and negative pressure, and/or the further incubation at higher heat, the meal fraction of oilseed and exogenous myrosinase can be continuously mixed.

In one embodiment, the invention provides the process described herein for removing at least one glucosinolate from a meal fraction of oilseed, wherein the process further comprises continuously mixing the meal fraction of oilseed and exogenous myrosinase during step (a) and step (b).

In another embodiment, the invention provides the process described herein for removing at least one glucosinolate from a meal fraction of oilseed, wherein the process further comprises continuously mixing the meal fraction of oilseed and exogenous myrosinase during step (a), step (b), and the post-treatment incubation.

In another embodiment, the invention provides the process described herein for removing at least one glucosinolate from a meal fraction of oilseed, wherein the process further comprises continuously mixing the meal fraction of oilseed and exogenous myrosinase during the post-treatment incubation.

Preheating

Prior to the steps of treating the meal fraction of oilseed with exogenous myrosinase to convert the at least one glucosinolate to a volatile isothiocyanate, and removing the volatile isothiocyanate from the treated meal fraction of oilseed under conditions of mild heat and negative pressure, the meal fraction of oilseed can be preheated.

In one embodiment, the invention provides the process described herein for removing at least one glucosinolate from a meal fraction of oilseed, wherein the process further comprises preheating the meal fraction of oilseed to between 25° C. to 40° C. prior to step (a).

In another embodiment, the invention provides the process described herein for removing at least one glucosinolate from a meal fraction of oilseed, wherein the process further comprises preheating the meal fraction of oilseed to between 30° C. to 40° C. prior to step (a).

In another embodiment, the invention provides the process described herein for removing at least one glucosinolate from a meal fraction of oilseed, wherein the process further comprises preheating the meal fraction of oilseed to 35° C. prior to step (a).

Myrosinase

Any exogenous myrosinase source can be used to convert glucosinolate into isothiocyanate. However, for reasons of economy, the source of exogenous myrosinase does not have to be highly purified and can consist simply of a slurry of readily available defatted meal in water, termed a "triggering solution". Any defatted meal wherein the myrosinase is still active can be used as the source of myrosinase in the triggering solution, including, for example, the meal of oilseeds of the Brassicaceae family, including, for example, *Sinapis alba* and *Brassica carinata*. The triggering solution may also comprise ascorbic acid. The triggering solution may be incubated at room temperature for a period of time prior to its addition to the meal cake.

In another embodiment, the triggering solution is mixed with water and ascorbic acid to form a slurry which is incubated at room temperature for a period of time subsequent to its addition to the meal cake.

In another embodiment, the invention provides the process described herein for removing at least one glucosinolate from a meal fraction of oilseed, wherein the process further comprises providing the exogenous myrosinase in the form of a triggering solution comprising a slurry of defatted meal in water.

In another embodiment, the invention provides the process described herein for removing at least one glucosinolate from a meal fraction of oilseed, wherein the process further comprises providing the exogenous myrosinase in the form of a triggering solution comprising a slurry of defatted meal in water, and wherein the defatted meal is derived from oilseed of a plant species of the Brassicaceae family.

In another embodiment, the invention provides the process described herein for removing at least one glucosinolate from a meal fraction of oilseed, wherein the process further comprises providing the exogenous myrosinase in the form of a triggering solution comprising a slurry of defatted meal in water, and wherein the defatted meal is derived from oilseed of *Sinapis alba* (White mustard; mustard seed flour).

In another embodiment, the invention provides the process described herein for removing at least one glucosinolate from a meal fraction of oilseed, wherein the process further comprises providing the exogenous myrosinase in the form of a triggering solution comprising a slurry of defatted meal in water, and wherein the defatted meal is derived from oilseed of *Brassica carinata*.

In another embodiment, the invention provides the process described herein for removing at least one glucosinolate from a meal fraction of oilseed, wherein the process further comprises providing the exogenous myrosinase in the form of a triggering solution comprising a slurry of defatted meal in water, and wherein the triggering solution further comprises ascorbic acid.

In another embodiment, the invention provides the process described herein for removing at least one glucosinolate from a meal fraction of oilseed, wherein the process further comprises providing the exogenous myrosinase in the form of a triggering solution comprising a slurry of defatted meal in water, wherein the triggering solution further comprises ascorbic acid, and wherein the defatted meal is present in a percent weight of 0.5%, 0.1%, 0.5%, 1%, 2%, 3%, 4%, 5%, 6%, 7%, 8%, 9%, 10%, 15%, or 20%, and the ascorbic acid is present in a percent weight of 0.001%, 0.005%, 0.01%, 0.02%, 0.03%, 0.04%, 0.05%, 0.06%, 0.07%, 0.08%, 0.09%, or 0.1%.

In another embodiment, the invention provides the process described herein for removing at least one glucosinolate from a meal fraction of oilseed, wherein the process further comprises providing the exogenous myrosinase in the form of a triggering solution comprising a slurry of defatted meal in water, wherein the triggering solution further comprises ascorbic acid, and wherein the triggering solution comprises the water, defatted meal, and ascorbic acid in a ratio of 100:5:0.045 w/w/w.

In another embodiment, the invention provides the process described herein for removing at least one glucosinolate from a meal fraction of oilseed, wherein the process further comprises providing the exogenous myrosinase in the form of a triggering solution comprising a slurry of defatted meal in water, and wherein the process further comprises mixing the triggering solution for between 5 min to 30 min at room temperature prior to treating the meal.

In another embodiment, the invention provides the process described herein for removing at least one glucosinolate from a meal fraction of oilseed, wherein the process further comprises providing the exogenous myrosinase in the form of a triggering solution comprising a slurry of defatted meal in water, wherein the triggering solution further comprises ascorbic acid, and wherein the process further comprises mixing the triggering solution for between 5 min to 30 min at room temperature prior to treating the meal.

In another embodiment, the invention provides the process described herein for removing at least one glucosinolate from a meal fraction of oilseed, wherein the process further comprises providing the exogenous myrosinase in the form of a triggering solution comprising a slurry of defatted meal in water, and wherein the process further comprises mixing the triggering solution for 15 min or 20 min at room temperature prior to treating the meal.

In another embodiment, the invention provides the process described herein for removing at least one glucosinolate from a meal fraction of oilseed, wherein the process further comprises providing the exogenous myrosinase in the form of a triggering solution comprising a slurry of defatted meal in water, wherein the triggering solution further comprises ascorbic acid, and wherein the process further comprises mixing the triggering solution for 15 min or 20 min at room temperature prior to treating the meal.

In a non-limiting, illustrative example, the defatted meal for the triggering solution can be prepared by grinding the seed in a blender, for example a Waring™ blender, at medium speed into a uniform meal (i.e. until no full seeds remain visible). The contents of the blender are then emptied into a metal sieving pan and placed on a heating plate set at between 40° C. to 90° C. for approximately 20 minutes. During this time, the ground seeds are mixed occasionally to prevent charring. The pan is then removed from the heat and allowed to cool at room temperature. Then, two volumes ground seed is mixed vigorously with one volume hexane in a bottle. The phases are allowed to separate, and the oil phase is removed while the solid meal fraction is re-extracted three additional times with the same volume of hexane as described. After the final extraction, the meal is removed from the bottle and allowed to air-dry in a fume cabinet overnight. The triggering solution can then be prepared by adding water, or by adding water and ascorbic acid.

Adulteration of the meal by addition of toxic or noxious chemical agents during the course of removing glucosinolates from the meal will greatly affect the downstream usage of the processed meal. One advantage of this process is that the triggering solution consists of only water, ascorbic acid and defatted meal, which are innocuous in terms of their potential for meal adulteration. In particular ascorbic acid has been shown to be a non-competitive activator of plant myrosinase and is required to maintain the activity of myrosinase during the process. Ascorbic acid is an inexpensive, readily available, food quality component used extensively in the food manufacturing and processing industry and does not detrimentally affect the quality of the processed meal. For example, Ascorbic Acid (Powder/USP/FCC) can be purchased from Fisher Chemical, catalogue number A62-212.

Buffering agents are not required for efficacy of the triggering solution. However, in one embodiment, the present invention provides the process described herein, wherein the triggering solution further comprises a buffer. In another embodiment, the present invention provides the process described herein, wherein the triggering solution further comprises a buffer, and wherein the buffer comprises 0.1M potassium phosphate, pH 6.5.

In another embodiment, the present invention provides a process for preparing the triggering solution comprising mixing mustard seed flour, water, and ascorbic acid in the ratio of 5 kg mustard seed flour to 100 kg water to 45 g ascorbic acid to form a slurry, and incubating the slurry at room temperature for 20 minutes prior to addition to the meal cake.

In another embodiment, the present invention provides a process for preparing the triggering solution comprising mixing 120 kg of soft water and 45 g of ascorbic acid in a tank of suitable size, adding 5 kg of defatted *Sinapis alba* meal, and mixing the resultant slurry for 15 minutes at room temperature.

In another embodiment, the present invention provides a process for preparing the triggering solution comprising mixing 120 kg of soft water and 45 g of ascorbic acid in a tank of suitable size, adding 5 kg of defatted *Sinapis alba* meal, and mixing the resultant slurry for 20 minutes at room temperature.

In another embodiment, the present invention provides a process for preparing the triggering solution comprising mixing 120 kg of soft water and 45 g of ascorbic acid in a tank of suitable size, adding 5 kg of defatted *Brassica carinata* meal, and mixing the resultant slurry for 15 minutes at room temperature.

In another embodiment, the present invention provides a process for preparing the triggering solution comprising mixing 120 kg of soft water and 45 g of ascorbic acid in a tank of suitable size, adding 5 kg of defatted *Brassica carinata* meal, and mixing the resultant slurry for 20 minutes at room temperature.

Treating with Exogenous Myrosinase

Myrosinase can be added to the meal fraction of oilseed in any format and amount that provides sufficient myrosinase activity to convert the glucosinolates in the meal fraction of oilseed to isothiocyanates within a reasonable time period.

In one embodiment, the invention provides the process described herein for removing at least one glucosinolate from a meal fraction of oilseed, wherein the process further comprises adding triggering solution to the meal fraction of oilseed to reach a final moisture content in the meal fraction of oilseed of 20% to 40%.

In another embodiment, the invention provides the process described herein for removing at least one glucosinolate from a meal fraction of oilseed, wherein the process further comprises adding triggering solution to the meal fraction of oilseed to reach a final moisture content in the meal fraction of oilseed of 30%.

In another embodiment, the invention provides the process described herein for removing at least one glucosinolate from a meal fraction of oilseed, wherein the process further comprises adding triggering solution to the meal fraction of oilseed in a ratio of 0.5:1, 0.55:1, 0.6:1, 0.65:1, or 0.7:1 (w/w) triggering solution: meal fraction of oilseed.

In another embodiment, the invention provides the process described herein for removing at least one glucosinolate from a meal fraction of oilseed, wherein the process further comprises adding triggering solution to the meal fraction of oilseed in a ratio of 125:200 (w/w) triggering solution: meal fraction of oilseed.

Formation of the Meal Fraction of Oilseed

The meal fraction of oilseed to be processed by the process described herein for removing at least one glucosinolate from a meal fraction of oilseed can be the by-product of any process for extracting oil from oilseeds.

In one embodiment, the invention provides the process described herein for removing at least one glucosinolate from a meal fraction of oilseed, wherein the meal to be treated consists of meal samples obtained from a commercial crushing and oil extraction process as defined above.

In another embodiment, the processes described herein can be applied to seed meals obtained from seeds of the Brassicaceae, based on treatment of an oilseed meal cake, obtained after hexane extraction or derived from a cold-press process.

(a) Hexane Extraction

In another embodiment, the invention provides the process described herein for removing at least one glucosinolate from a meal fraction of oilseed, wherein the meal fraction of oilseed results from hexane extraction of oilseeds.

In another embodiment, the invention provides the process described herein for removing at least one glucosinolate from a meal fraction of oilseed, wherein the meal fraction of oilseed results from hexane extraction of oilseeds, and wherein the oilseeds were flaked and cooked prior to hexane extraction.

In another embodiment, the invention provides the process described herein for removing at least one glucosinolate from a meal fraction of oilseed, wherein the meal fraction of oilseed results from hexane extraction of oilseeds, wherein the oilseeds were flaked and cooked prior to hexane extraction, and wherein the cooking was carried out at a temperature greater than 70° C., 75° C., 80° C., 85° C., 90° C., 95° C., 100° C., 105° C., 110° C., 115° C., 120° C., 125° C., 130° C., 135° C., or 140° C., but less than 150° C., 155° C., 160° C., 165° C., 170° C., 175° C., or 180° C.

In another embodiment, the invention provides the process described herein for removing at least one glucosinolate from a meal fraction of oilseed, wherein the meal fraction of oilseed results from hexane extraction of oilseeds, wherein the oilseeds were flaked and cooked prior to hexane extraction, and wherein the duration of cooking was at least 10, 12, 14, 15, 16, 17, 18, 19, 20, 22, 24, 26, 28, or 30 minutes, but less than 60, 70, 80, 90, or 100 minutes.

In another embodiment, the invention provides the process described herein for removing at least one glucosinolate from a meal fraction of oilseed, wherein the meal fraction of oilseed results from hexane extraction of oilseeds, wherein the oilseeds were flaked and cooked prior to hexane extraction, and wherein the flaked and cooked oilseeds were crushed to leave a meal cake with the bulk of the oil removed prior to hexane extraction.

In another embodiment, the invention provides the process described herein for removing at least one glucosinolate from a meal fraction of oilseed, wherein the meal fraction of oilseed results from hexane extraction of oilseeds, wherein the oilseeds were flaked and cooked prior to hexane extraction, and wherein the flaked and cooked oilseeds were crushed using an expeller or a screw press prior to hexane extraction.

In another embodiment, the invention provides the process described herein for removing at least one glucosinolate from a meal fraction of oilseed, wherein the meal fraction of oilseed results from hexane extraction of oilseeds, wherein the oilseeds were flaked and cooked prior to hexane extraction, and wherein the flaked and cooked oilseeds were crushed using an expeller prior to hexane extraction.

In another embodiment, the invention provides the process described herein for removing at least one glucosinolate from a meal fraction of oilseed, wherein the meal fraction of oilseed results from hexane extraction of oilseeds, wherein the oilseeds were flaked and cooked prior to hexane extraction, and wherein the flaked and cooked oilseeds were crushed using a screw press prior to hexane extraction.

In another embodiment, the invention provides the process described herein for removing at least one glucosinolate from a meal fraction of oilseed, wherein the meal fraction of oilseed results from countercurrent hexane extraction of oilseeds.

In another embodiment, the invention provides the process described herein for removing at least one glucosinolate from a meal fraction of oilseed, wherein the meal fraction of oilseed results from hexane extraction of oilseeds, and wherein the meal fraction of oilseed is hexane-extracted meal treated in a desolventizer-toaster (DT) to remove the residual hexane.

In another embodiment, the invention provides the process described herein for removing at least one glucosinolate from a meal fraction of oilseed, wherein the meal fraction of oilseed results from hexane extraction of oilseeds, wherein the meal fraction of oilseed is hexane-extracted meal treated in a desolventizer-toaster (DT) to remove the residual hexane, and wherein the treatment in the DT was at a temperature of at least 50° C., 55° C., 60° C., 65° C., 70° C., 75° C., 80° C., 85° C., 90° C., 95° C., 100° C., 105° C., 110° C., 115° C., 120° C., 125° C., or 130° C., but less 130° C., than 135° C., 140° C., 145° C., or 150° C.

In another embodiment, the invention provides the process described herein for removing at least one glucosinolate from a meal fraction of oilseed, wherein the meal fraction of oilseed results from hexane extraction of oilseeds, wherein the meal fraction of oilseed is hexane-extracted meal treated in a desolventizer-toaster (DT) to remove the residual hexane, and wherein the meal fraction of oilseed is hexane-extracted, desolventizer-toaster-treated meal dried to less than 12% humidity.

In another embodiment, the invention provides the process described herein for removing at least one glucosinolate from a meal fraction of oilseed, wherein the process further comprises producing the meal to be treated by hexane extracting oilseeds.

In another embodiment, the invention provides the process described herein for removing at least one glucosinolate from a meal fraction of oilseed, wherein the process further comprises producing the meal to be treated by hexane extracting oilseeds, and flaking the oilseed prior to cooking for hexane extraction.

In another embodiment, the invention provides the process described herein for removing at least one glucosinolate from a meal fraction of oilseed, wherein the process further comprises producing the meal to be treated by hexane extracting oilseeds, flaking the oilseed prior to cooking for hexane extraction, and cooking the flaked oilseed at a temperature greater than 70° C., 75° C., 80° C., 85° C., 90° C., 95° C., 100° C., 105° C., 110° C., 115° C., 120° C., 125° C., 130° C., 135° C., or 140° C., but less than 150° C., 155° C., 160° C., 165° C., 170° C., 175° C., or 180° C. prior to hexane extraction.

In one such embodiment, the invention provides the process described herein, wherein the process further comprises pretreating and flaking the oilseeds at 85-95° C. prior to hexane extraction. In another such embodiment, the invention provides the process described herein, wherein the process further comprises pretreating and flaking the oilseeds at 105° C. or higher prior to hexane extraction. In the latter embodiment, the glucosinolate levels of the meal cake may be reduced substantially from that of meal cake obtained from a process as outlined in the former embodiment.

In another embodiment, the invention provides the process described herein for removing at least one glucosinolate from a meal fraction of oilseed, wherein the process further comprises producing the meal to be treated by hexane extracting oilseeds, flaking the oilseed prior to cooking for hexane extraction, and cooking the flaked oilseed for at least 10, 12, 14, 15, 16, 17, 18, 19, 20, 22, 24, 26, 28 or 30 minutes, but less than 60, 70, 80, 90, or 100 minutes prior to hexane extraction.

In another embodiment, the invention provides the process described herein for removing at least one glucosinolate from a meal fraction of oilseed, wherein the process further comprises producing the meal to be treated by hexane extracting oilseeds, flaking the oilseed prior to cooking for hexane extraction, and crushing the flaked, cooked oilseed to leave a meal cake with the bulk of the oil removed prior to the hexane extraction.

In another embodiment, the invention provides the process described herein for removing at least one glucosinolate from a meal fraction of oilseed, wherein the process further comprises producing the meal to be treated by hexane extracting oilseeds, flaking the oilseed prior to cooking for hexane extraction, and pressing the flaked and cooked oilseed through an expeller or a screw press prior to hexane extraction.

In another embodiment, the invention provides the process described herein for removing at least one glucosinolate from a meal fraction of oilseed, wherein the process further comprises treating the meal cake by countercurrent hexane extraction to remove remaining oil.

In another embodiment, the invention provides the process described herein for removing at least one glucosinolate from a meal fraction of oilseed, wherein the process further comprises producing the meal to be treated by hexane extracting oilseeds, and treating the hexane-extracted meal cake in a desolventizer-toaster (DT) to remove the residual hexane prior to treating the meal with exogenous myrosinase.

In another embodiment, the invention provides the process described herein for removing at least one glucosinolate from a meal fraction of oilseed, wherein the process further comprises producing the meal to be treated by hexane extracting oilseeds, and treating the hexane-extracted meal cake in a desolventizer-toaster (DT) to remove the residual hexane prior to treating the meal with exogenous myrosinase, and wherein the treatment in the DT is at a temperature of at least 50° C. 55° C., 60° C., 65° C., 70° C., 75° C., 80° C., 85° C., 90° C., 95° C. 100° C. 95° C., 100° C., 105° C., 110° C., 115° C., 120° C., 125° C., 130° C., but less than 135° C., 140° C., 145° C., or 150° C.

In another embodiment, the invention provides the process described herein for removing at least one glucosinolate from a meal fraction of oilseed, wherein the process further comprises producing the meal to be treated by hexane extracting oilseeds, treating the hexane-extracted meal cake in a desolventizer-toaster (DT) to remove the residual hexane prior to treating the meal with exogenous myrosinase, and drying the hexane-extracted, desolventizer-toaster-treated meal cake to less than 12% humidity prior to treating the meal with exogenous myrosinase.

(b) Cold Press Processing

In another embodiment, the invention provides the process described herein for removing at least one glucosinolate from a meal fraction of oilseed, wherein the meal fraction of oilseed results from cold press processing of oilseeds.

In another embodiment, the invention provides the process described herein for removing at least one glucosinolate from a meal fraction of oilseed, wherein the process further comprises producing the meal fraction of oilseeds by a cold press process.

Preparing the Meal Fraction of Oilseeds for Processing

In another embodiment, the invention provides the process described herein for removing at least one glucosinolate from a meal fraction of oilseed, wherein the process further comprises carrying out the treatment as a batch process on a meal cake, comprising glucosinolate. In such an embodiment, the meal cake should be of a consistency that would allow for optimal penetration of a triggering solution.

In another embodiment, the invention provides the process described herein for removing at least one glucosinolate from a meal fraction of oilseed, wherein the meal fraction of oilseed to be treated is pelleted.

In another embodiment, the invention provides the process described herein for removing at least one glucosinolate from a meal fraction of oilseed, wherein the meal fraction of oilseed to be treated is pelleted, and wherein the pelleted meal fraction of oilseed is homogenized by hammer-milling.

In another embodiment, the invention provides the process described herein for removing at least one glucosinolate from a meal fraction of oilseed, wherein the meal fraction of oilseed to be treated is pelleted, wherein the pelleted meal fraction of oilseed is homogenized by hammer-milling, and wherein the homogenized meal fraction of oilseed has a size of less than 5.66 mm, 4.75 mm, 4.00 mm, 3.36 mm, 2.83 mm or 2.38 mm.

In another embodiment, the invention provides the process described herein for removing at least one glucosinolate from a meal fraction of oilseed, wherein the meal fraction of oilseed to be treated is pelleted, wherein the pelleted meal fraction of oilseed is homogenized by hammer-milling, and wherein the homogenized meal fraction of oilseed has a size of less than 3.36 mm.

In another embodiment, the present invention provides the process described herein, wherein the meal to be treated is finely granular meal. Finely granular meal can be prepared from pelleted meal by homogenizing with a hammer mill (such as Model G5HFS1, serial number 5075, Prater Industries, Chicago IL). The hammer mill can be equipped with ⅜₄" screens, which is standard equipment in a seed crushing plant.

In one such embodiment, the invention provides the process described herein for removing at least one glucosinolate from a meal fraction of oilseed, wherein the process further comprises applying the processes to pelleted meal that was processed in a hammer mill equipped with screens of ⅜₄" to obtain a suitable consistency prior to application of the batch process.

In another embodiment, the invention provides the process described herein for removing at least one glucosinolate from a meal fraction of oilseed, wherein the process further comprises pelleting the meal fraction of oilseed prior to step (a).

In another embodiment, the invention provides the process described herein for removing at least one glucosinolate from a meal fraction of oilseed, wherein the process further comprises homogenizing the pelleted meal with a hammer mill prior to step (a).

In another embodiment, the invention provides the process described herein for removing at least one glucosinolate from a meal fraction of oilseed, wherein the process further comprises homogenizing the pelleted meal to a size of less than 5.66 mm, 4.75 mm, 4.00 mm, 3.36 mm, 2.83 mm, or 2.38 mm, prior to step (a).

In another embodiment, the invention provides the process described herein for removing at least one glucosinolate from a meal fraction of oilseed, wherein the process further comprises homogenizing the pelleted meal to a size less than 3.36 mm, prior to step (a).

Oilseeds

The meal fraction of any oilseed that has glucosinolates can be used as the substrate from the process described herein for removing at least one glucosinolate from a meal fraction of oilseed.

In one embodiment, the invention provides the process described herein for removing at least one glucosinolate from a meal fraction of oilseed, wherein the meal fraction of oilseed is from oilseed of a plant species of the family Brassicaceae.

In another embodiment, the invention provides the process described herein for removing at least one glucosinolate from a meal fraction of oilseed, wherein the meal fraction of oilseed is from oilseed of *Brassica juncea, Brassica napus, Brassica rapa, Brassica carinata, Brassica nigra, Cammelina sativa, Crambe abyssinica*, or *Thlaspi arvense*.

In another embodiment, the invention provides the process described herein for removing at least one glucosinolate from a meal fraction of oilseed, wherein the meal fraction of oilseed is from oilseed of *Brassica carinata*.

With respect to *Brassica carinata* under the reaction conditions cited above, the added myrosinase converts sinigrin to allyl-isothiocyanate. In a novel aspect of this invention which relies on the low vapor pressure (high volatility) of allyl-isothiocyanate, the vessel temperature is then adjusted and the vessel allowed to vent under negative pressure, permitting the bulk of the volatile allyl-isothiocyanate to be removed from the vessel. As a result of such treatment, meal with substantially reduced glucosinolate content is derived as exemplified below.

In another embodiment, the invention provides the process described herein for removing at least one glucosinolate from a meal fraction of oilseed, wherein the meal fraction of oilseed is from oilseed of *Sinapis alba*.

In another embodiment, the present invention provides the process described herein, wherein the meal fraction of oilseeds is from *Camelina sativa* (false flax), *Crambe abyssinica* (Crambe) or *Thlaspi arvense* (pennycress).

In another embodiment, the present invention provides the process described herein, wherein the meal fraction of oilseeds is from double zero quality canola meal, and wherein the process reduces the existing low levels of glucosinolates to non-detectable levels.

Reaction Vessel

In one embodiment, the invention provides the process described herein for removing at least one glucosinolate from a meal fraction of oilseed, wherein the process further comprises carrying out the treatment and/or post-treatment incubation in a reaction vessel equipped to allow for continuous mixing of its contents, regulation of the internal temperature of the vessel contents, and venting to allow for separating and removing volatiles or gaseous products from the contents of the vessel.

In another embodiment, the processes described herein further comprise a treatment of a seed meal cake containing glucosinolate, wherein the treatment involves incubating the meal with an exogenous source of myrosinase, wherein the hydrolysis product is substantially removed from the seed meal cake by virtue of its high volatility, and wherein the removal of the isothiocyanate component of the reaction is facilitated by application of reduced pressure to the reaction vessel.

In another embodiment, the invention provides the process described herein for removing at least one glucosinolate from a meal fraction of oilseed, wherein the removal of glucosinolates from the meal is initiated by addition of the triggering solution to the bulk of the meal. The granular meal is then added, along with the triggering solution, to a closed reaction vessel of suitable size and configuration, equipped with a plough type mixer, heating and cooling capability to allow maintenance of internal temperatures through a range of 35° C. to 70° C., and exhaust ports that can allow the chamber to be vented under negative pressure.

In another embodiment, the invention provides the process described herein for removing at least one glucosinolate from a meal fraction of oilseed, wherein the reaction vessel is a desolventizer-toaster, and wherein step (a), step (b), and the further incubation are part of a desolventizer-toaster step of hexane extraction of oilseeds.

An example of a reaction vessel that can be used for the present invention is a Littleford™ vacuum dryer (Littleford Reactor™ 600 liter model FKM600-D 2Z, serial number 5132, Littleford-Day Inc., Florence, KY).

Figure 2:
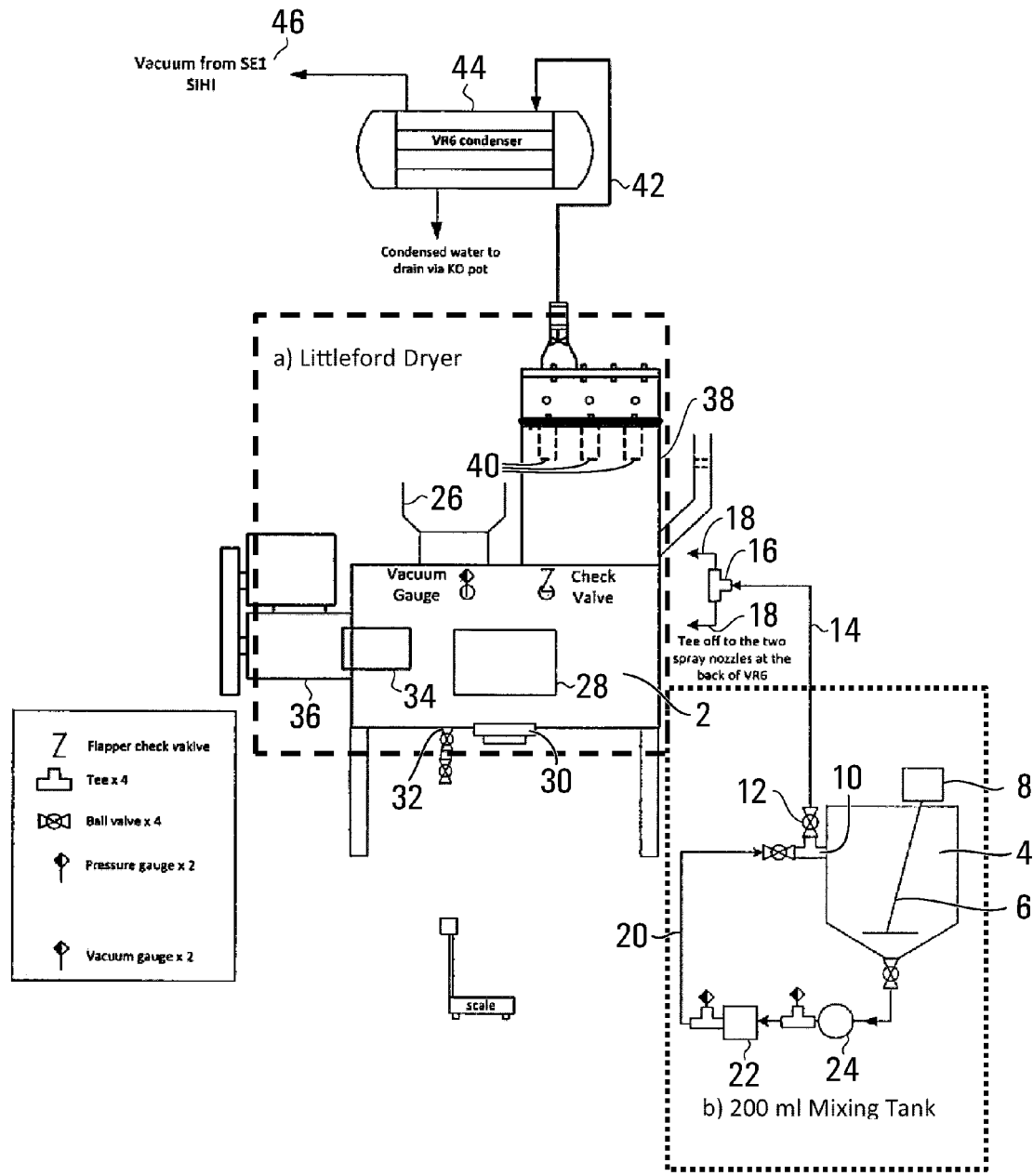
FIG. 2 is a schematic diagram of an illustrative apparatus that may be used for the batchwise removal of glucosinolate from oilseed meal.

FIG. 2 is a schematic diagram of a Littleford™ vacuum dryer apparatus that can be used for the batchwise removal of glucosinolate oilseed meal. In a non-limiting, illustrative example, two hundred kilograms of oilseed meal is placed in reaction vessel 2. The plough mixer (not visible), connected to its drive unit 36 by coupler 34, is started and the meal is heated to 35° C. At the same time, 120 kg of soft water is loaded into the 200 liter stainless steel mixing vessel 4 and 45 g of ascorbic acid is added. After 5 minutes of mixing the water and ascorbic acid with agitator 6 driven by motor 8, 5 kg of defatted oilseed meal is added to the mixing vessel 4 to form the triggering solution. The triggering solution is circulated via an inline mixer, comprising piping 20 attached to a recirculation pump 22 downstream of drain 24, for 20 minutes and then sprayed into the reaction vessel 2. The inline mixer and the mixing vessel 4 are attached to the reaction vessel 2 via a tee 10, a ball valve 12, piping 14, spray tee 16, and two spray nozzles 18. The dispensing of the slurry comprising the triggering solution requires a spray head that will not be clogged by the granular nature of the slurry.

At the top of the reaction vessel 2 is a hatch 26 through which the material (e.g. meal) is added to the chamber. The reaction vessel 2 also has a chamber access hatch 28, a discharge hatch 30 for removal of the processed material, and a bottom port 32, with a double valve system with a reducer in between, for sampling from the chamber.

At the right-hand side of the top of the reaction vessel 2, the reaction vessel 2 is attached to a bag housing 38 containing three bags 40. The bags are filters that isolate the contents of the chamber from the vacuum source 46/condenser 44, allowing the vapour to go through but keeping the dust and particulates confined to the reaction vessel side. Vacuum line 42 is attached to a condenser 44. The vacuum source 46 is a steam ejector (SE1 SIHI).

In one embodiment, the present invention provides the process described herein, wherein the triggering solution is allowed to react with the oilseed for 3 hours in reaction vessel 2. It can be appreciated that during this time the temperature will rise during the course of the reaction, to achieve a temperature of 45° C. to 50° C. by the end of the three hour incubation. During this time the bulk of the glucosinolate is converted to isothiocyanate. At the completion of the reaction, the temperature in the reaction vessel 2 is raised to 60° C. to 70° C. to allow for drying of the meal to less than 12% retained humidity.

In another embodiment, the present invention provides the process described herein, wherein vacuum is applied to the reaction vessel 2 and the meal is then heated to 50° C. for an additional one hour. After the one hour hold at 50° C., the meal is heated to 70° C. to 74° C. and dried to a moisture content of <12%.

In another embodiment, the present invention provides the process described herein, wherein vacuum is applied to reaction vessel 2 from the onset of the initial treatment.

In another embodiment, the present invention provides the process described herein, wherein the contents of the reaction vessel 2 are initially adjusted to 35° C., prior to the addition of the triggering solution.

The myrosinase catalyzed hydrolysis of glucosinolate is a highly exothermic reaction and therefore once the reaction has commenced (by spraying the triggering solution onto the meal sample), cooling water is circulated in the jacket (not visible) of the reaction vessel 2 to allow for dissipation of the heat produced during the reaction. The reaction is allowed to proceed for a period of time sufficient to allow for substantial conversion of the glucosinolate to isothiocyanate.

In one embodiment, the present invention provides the process described herein, wherein cooling water is circulated in the jacket (not visible) of reaction vessel 2 from the outset of the reaction to allow attainment of a maximum temperature at 50° C. -60° C. during the three hour reaction.

In another embodiment, the present invention provides the process described herein, wherein cooling water is circulated in the jacket (not visible) of reaction vessel 2 only once the temperature in the chamber had reached 35° C. during the initial reaction.

In another embodiment, the present invention provides the process described herein, wherein the meal undergoing the process is obtained from *Brassica carinata*, which contains sinigrin (2-propylglucosinolate) as the predominant glucosinolate species, which is converted to allyl isothiocyanate, a volatile, extremely pungent and potent lachrymator, by the action of myrosinase. In the examples provided, volatile allyl isothiocyanate released by the reaction is vented to the exterior of the reaction vessel 2. A steam ejector vacuum source 46 applied to the reaction vessel 2 while venting allows for improved efficiency of allyl isothiocyanate removal from the vessel during the three hour course of the reaction and subsequent meal drying step. An advantage of maintaining the vacuum is that the negative pressure coupled with the rising temperature in the chamber and the higher temperatures during the drying step, leads to more complete removal of the produced allyl isothiocyanate than would normally be achievable, thus eliminating the requirement for auxiliary means of isothiocyanate removal, such as those outlined previously, which can adversely affect the quality of the processed meal. As a result of such treatment, meal with substantially reduced glucosinolate content is derived as exemplified below. The substantial reduction in glucosinolate may result in the meal having less than 80% of their starting levels of glucosinolates.

In a non-limiting, illustrative example, the present invention provides a process comprising preparing a triggering solution of mustard seed flour, water and ascorbic acid in the ratio of 5 kg mustard seed flour to 100 kg water to 45 g ascorbic acid, and incubating the slurry at room temperature for 20 minutes prior to addition the meal cake; spraying the triggering solution onto hammer milled meal contained in a reaction vessel of suitable size and capable of both heating and mixing as well as venting to allow for removal of volatiles (e.g. a Littleford™ vacuum dryer); and incubating with continuous mixing at an appropriate temperature and for an appropriate time.

Inline Removal of Glucosinolate During the Desolventizer-Toaster Step of Hexane Extraction While the examples cited herein describe a process which is adapted to batch processing of meal samples, the process can be adapted so that it can function "inline" of an existing oilseed crushing/hexane extraction processing plant such as that described earlier. In particular, there is ample opportunity to incorporate the process with very little disruption or cost into the desolventizer-toaster stage, which can readily be adapted for the mixing, temperature regulation and venting described for the batch glucosinolate removal process.

In one embodiment, the process described herein is incorporated into an existing seed crushing line, to provide a continuous process such as was described in the background section.

In one embodiment, the invention provides a process for removing at least one glucosinolate from a meal fraction of oilseed at the desolventizer-toaster step of a hexane extraction process, comprising: (a) treating the meal fraction of oilseed with exogenous myrosinase, to convert the at least one glucosinolate to volatile isothiocyanate; and (b) removing the volatile isothiocyanate from the treated meal fraction of oilseed under conditions of mild heat and negative pressure during desolventizing and toasting.

In another embodiment, the invention provides the process described herein for removing at least one glucosinolate from a meal fraction of oilseed at the desolventizer-toaster step of a hexane extraction process, wherein step (a) and step (b) occur simultaneously.

In another embodiment, the invention provides the process described herein for removing at least one glucosinolate from a meal fraction of oilseed at the desolventizer-toaster step of a hexane extraction process, wherein step (a) and step (b) occur sequentially.

In another embodiment, the invention provides the process described herein for removing at least one glucosinolate from a meal fraction of oilseed at the desolventizer-toaster step of a hexane extraction process, wherein the process further comprises continuously mixing the meal fraction of oilseed and exogenous myrosinase during step (a) and step (b).

In another embodiment, the invention provides the process described herein for removing at least one glucosinolate from a meal fraction of oilseed at the desolventizer-toaster step of a hexane extraction process, wherein the desolventizing and toasting time of step (b) is greater than 2 min, 5 min, 10 min, 15 min, 20 min, 25 min, 30 min, 35 min, 40 min, 50 min, or 1 h, but less than 1.5 h, 2 h, 3 h, 4 h, or 5 h.

In another embodiment, the invention provides the process described herein for removing at least one glucosinolate from a meal fraction of oilseed at the desolventizer-toaster step of a hexane extraction process, wherein the desolventizing and toasting time of step (b) is 20 min.

In another embodiment, the invention provides the process described herein for removing at least one glucosinolate from a meal fraction of oilseed at the desolventizer-toaster step of a hexane extraction process, wherein the desolventizing and toasting time of step (b) is 30 min.

In another embodiment, the invention provides the process described herein for removing at least one glucosinolate from a meal fraction of oilseed at the desolventizer-toaster step of a hexane extraction process, wherein the process further comprises drying the meal fraction of oilseed until the moisture content of the meal decreases to less than 20%, 18%, 16%, 14%, 12% or 10%.

In another embodiment, the invention provides the process described herein for removing at least one glucosinolate from a meal fraction of oilseed at the desolventizer-toaster step of a hexane extraction process, wherein the process further comprises drying the meal fraction of oilseed until the moisture content of the meal decreases to less than 12%.

In another embodiment, the invention provides the process described herein for removing at least one glucosinolate from a meal fraction of oilseed at the desolventizer-toaster step of a hexane extraction process, wherein the process further comprises carrying out the desolventizing and toasting in a desolventizer-toaster under negative pressure and evacuating volatile substances from the desolventizer-toaster.

In another embodiment, the invention provides the process described herein for removing at least one glucosinolate from a meal fraction of oilseed at the desolventizer-toaster step of a hexane extraction process, wherein the desolventizer-toaster is under negative pressure of over 10%, 20%, 30%, 40%, 50%, 60%, 70%, 80%, 90%, 95%, 98%, or 99% vacuum.

In another embodiment, the invention provides the process described herein for removing at least one glucosinolate from a meal fraction of oilseed at the desolventizer-toaster step of a hexane extraction process, wherein the process further comprises providing the exogenous myrosinase in the form of a triggering solution comprising a slurry of defatted meal in water.

In another embodiment, the invention provides the process described herein for removing at least one glucosinolate from a meal fraction of oilseed at the desolventizer-toaster step of a hexane extraction process, wherein the process further comprises providing the exogenous myrosinase in the form of a triggering solution comprising a slurry of defatted meal in water, and wherein the defatted meal is from oilseed of a plant species of the Brassicaceae family.

In another embodiment, the invention provides the process described herein for removing at least one glucosinolate from a meal fraction of oilseed at the desolventizer-toaster step of a hexane extraction process, wherein the process further comprises providing the exogenous myrosinase in the form of a triggering solution comprising a slurry of defatted meal in water, and wherein the defatted meal is from oilseed of *Sinapis alba*.

In another embodiment, the invention provides the process described herein for removing at least one glucosinolate from a meal fraction of oilseed at the desolventizer-toaster step of a hexane extraction process, wherein the process further comprises providing the exogenous myrosinase in the form of a triggering solution comprising a slurry of defatted meal in water, and wherein the defatted meal is from oilseed of *Brassica carinata*.

In another embodiment, the invention provides the process described herein for removing at least one glucosinolate from a meal fraction of oilseed at the desolventizer-toaster step of a hexane extraction process, wherein the process further comprises providing the exogenous myrosinase in the form of a triggering solution comprising a slurry of defatted meal in water, and wherein the triggering solution further comprises ascorbic acid.

In another embodiment, the invention provides the process described herein for removing at least one glucosinolate from a meal fraction of oilseed at the desolventizer-toaster step of a hexane extraction process, wherein the process further comprises providing the exogenous myrosinase in the form of a triggering solution comprising a slurry of defatted meal in water, wherein the triggering solution further comprises ascorbic acid, and wherein the defatted meal is present in a percent weight of 0.5%, 0.1%, 0.5%, 1%, 2%, 3%, 4%, 5%, 6%, 7%, 8%, 9%, 10%, 15%, or 20%, and the ascorbic acid is present in a percent weight of 0.001%, 0.005%, 0.01%, 0.02%, 0.03%, 0.04%, 0.05%, 0.06%, 0.07%, 0.08%, 0.09%, or 0.1%.

In another embodiment, the invention provides the process described herein for removing at least one glucosinolate from a meal fraction of oilseed at the desolventizer-toaster step of a hexane extraction process, wherein the process further comprises providing the exogenous myrosinase in the form of a triggering solution comprising a slurry of defatted meal in water, and wherein the triggering solution comprises the water, defatted meal, and ascorbic acid in a ratio of 100:5:0.045 w/w/w.

In another embodiment, the invention provides the process described herein for removing at least one glucosinolate from a meal fraction of oilseed at the desolventizer-toaster step of a hexane extraction process, wherein the process further comprises providing the exogenous myrosinase in the form of a triggering solution comprising a slurry of defatted meal in water, and wherein the process further comprises mixing the triggering solution for between 5 min to 30 min at room temperature prior to treating the meal fraction of oilseed.

In another embodiment, the invention provides the process described herein for removing at least one glucosinolate from a meal fraction of oilseed at the desolventizer-toaster step of a hexane extraction process, wherein the process further comprises providing the exogenous myrosinase in the form of a triggering solution comprising a slurry of defatted meal in water, and wherein the process further comprises adding triggering solution to the meal fraction of oilseed to reach a final moisture content in the meal fraction of oilseed of 20% to 40%.

In another embodiment, the invention provides the process described herein for removing at least one glucosinolate from a meal fraction of oilseed at the desolventizer-toaster step of a hexane extraction process, wherein the process further comprises providing the exogenous myrosinase in the form of a triggering solution comprising a slurry of defatted meal in water, and wherein the process further comprises adding triggering solution to the meal fraction of oilseed to reach a final moisture content in the meal fraction of oilseed of 30%.

In another embodiment, the invention provides the process described herein for removing at least one glucosinolate from a meal fraction of oilseed at the desolventizer-toaster step of a hexane extraction process, wherein the process further comprises providing the exogenous myrosinase in the form of a triggering solution comprising a slurry of defatted meal in water, and wherein the process further comprises adding triggering solution to the meal fraction of oilseed in a ratio of 0.5:1, 0.55:1, 0.6:1, 0.65:1, or 0.7:1 (w/w) triggering solution: meal fraction of oilseed.

In another embodiment, the invention provides the process described herein for removing at least one glucosinolate from a meal fraction of oilseed at the desolventizer-toaster step of a hexane extraction process, wherein the process further comprises providing the exogenous myrosinase in the form of a triggering solution comprising a slurry of defatted meal in water, and wherein the process further comprises adding triggering solution to the meal fraction of oilseed in a ratio of 125:200 (w/w) triggering solution: meal fraction of oilseed.

In another embodiment, the invention provides the process described herein for removing at least one glucosinolate from a meal fraction of oilseed at the desolventizer-toaster step of a hexane extraction process, wherein the oilseeds were flaked and cooked prior to hexane extraction.

In another embodiment, the invention provides the process described herein for removing at least one glucosinolate from a meal fraction of oilseed at the desolventizer-toaster step of a hexane extraction process, wherein the oilseeds were flaked and cooked prior to hexane extraction, and wherein the cooking was carried out at a temperature greater than 70° C., 75° C., 80° C., 85° C., 90° C., 95° C., 100° C., 105° C., 110° C., 115° C., 120° C., 125° C., 130° C., 135° C., or 140° C., but less than 150° C., 155° C., 160° C., 165° C., 170° C., 175° C., or 180° C.

In another embodiment, the invention provides the process described herein for removing at least one glucosinolate from a meal fraction of oilseed at the desolventizer-toaster step of a hexane extraction process, wherein the oilseeds were flaked and cooked prior to hexane extraction, and wherein the duration of cooking was at least 10, 12, 14, 15, 16, 17, 18, 19, 20, 22, 24, 26, 28, or 30 minutes, but less than 60, 70, 80, 90, or 100 minutes.

In another embodiment, the invention provides the process described herein for removing at least one glucosinolate from a meal fraction of oilseed at the desolventizer-toaster step of a hexane extraction process, wherein the hexane extraction was carried out on flaked and cooked oilseed that had been crushed using an expeller or a screw press.

In another embodiment, the invention provides the process described herein for removing at least one glucosinolate from a meal fraction of oilseed at the desolventizer-toaster step of a hexane extraction process, wherein the hexane extraction was carried out on flaked and cooked oilseed that had been crushed using an expeller.

In another embodiment, the invention provides the process described herein for removing at least one glucosinolate from a meal fraction of oilseed at the desolventizer-toaster step of a hexane extraction process, wherein the hexane extraction was carried out on flaked and cooked oilseed that had been crushed using a screw press.

In another embodiment, the invention provides the process described herein for removing at least one glucosinolate from a meal fraction of oilseed at the desolventizer-toaster step of a hexane extraction process, wherein the oilseeds were flaked and cooked prior to hexane extraction, and wherein the flaked, cooked oilseeds were crushed to leave a meal cake with the bulk of the oil removed prior to hexane extraction.

In another embodiment, the invention provides the process described herein for removing at least one glucosinolate from a meal fraction of oilseed at the desolventizer-toaster step of a hexane extraction process, wherein the meal fraction of oilseed results from countercurrent hexane extraction of oilseeds.

In another embodiment, the invention provides the process described herein for removing at least one glucosinolate from a meal fraction of oilseed at the desolventizer-toaster step of a hexane extraction process, wherein the meal fraction of oilseed is from oilseed of a plant species of the family Brassicaceae.

In another embodiment, the invention provides the process described herein for removing at least one glucosinolate from a meal fraction of oilseed at the desolventizer-toaster step of a hexane extraction process, wherein the meal fraction of oilseed is from oilseed of *Brassica juncea, Brassica napus, Brassica rapa, Brassica carinata, Brassica nigra, Cammelina sativa, Crambe abyssinica*, or *Thlaspi arvense*.

In another embodiment, the invention provides the process described herein for removing at least one glucosinolate from a meal fraction of oilseed at the desolventizer-toaster step of a hexane extraction process, wherein the meal fraction of oilseed is from oilseed of *Brassica carinata*.

In another embodiment, the invention provides the process described herein for removing at least one glucosinolate from a meal fraction of oilseed at the desolventizer-toaster step of a hexane extraction process, wherein the meal fraction of oilseed is from oilseed of *Sinapis alba*.

Removal of Glucosinolates from *Brassica Carinata* using Heat and Pressure

*Brassica carinata* seed is unique, because it has a lower fibre and a higher protein content than other Brassica seeds, and also has a thinner seed coat. In addition, current commercial varieties of *Brassica carinata* seed contain different levels and types of glucosinates than other members of the Brassicaceae family. For example, *Brassica carinata* seed has higher overall levels of glucosinates, with the predominant form being sinigrin, than *Brassica napus*, which has little or no sinigrin (Xin et al., 2014). Therefore, *Brassica carinata* seed will process differently than other Brassica seeds, and it is not predictable how *Brassica carinata* seeds will respond to techniques used on other Brassica species.

In another embodiment, the present invention provides a process for removing at least one glucosinolate from a meal fraction of a *Brassica carinata* oilseed comprising heating and applying pressure to the oilseed before, during, or after the extraction of oil.

In another embodiment, the present invention provides the process described herein for removing at least one glucosinolate from a meal fraction of a *Brassica carinata* oilseed comprising heating and applying pressure to the oilseed before, during, or after the extraction of oil, wherein the temperature during heating is greater than 70° C., 75° C., 80° C., 85° C., 90° C., 95° C., 100° C., 105° C., 110° C., 115° C., 120° C., 125° C., 130° C., 135° C., or 140° C., but less than 150° C., 155° C., 160° C., 165° C., 170° C., 175° C., or 180° C.

In another embodiment, the present invention provides the process described herein for removing at least one glucosinolate from a meal fraction of a *Brassica carinata* oilseed comprising heating and applying pressure to the oilseed before, during, or after the extraction of oil, wherein the duration of heating is at least 10, 12, 14, 15, 16, 17, 18, 19, 20, 22, 24, 26, 28, or 30 minutes, but less than 60, 70, 80, 90, or 100 minutes.

In another embodiment, the present invention provides the process described herein for removing at least one glucosinolate from a meal fraction of a *Brassica carinata* oilseed comprising heating and applying pressure to the oilseed before, during, or after the extraction of oil, wherein the process further comprises applying the pressure using an expeller or a screw press.

In another embodiment, the present invention provides the process described herein for removing at least one glucosinolate from a meal fraction of a *Brassica carinata* oilseed comprising heating and applying pressure to the oilseed before, during, or after the extraction of oil, wherein the process further comprises applying the pressure using an expeller.

In another embodiment, the present invention provides the process described herein for removing at least one glucosinolate from a meal fraction of a *Brassica carinata* oilseed comprising heating and applying pressure to the oilseed before, during, or after the extraction of oil, wherein the process further comprises applying the pressure using a screw press.

In another embodiment, the present invention provides the process described herein for removing at least one glucosinolate from a meal fraction of a *Brassica carinata* oilseed comprising heating and applying pressure to the oilseed before, during, or after the extraction of oil, wherein the process results in a reduction of glucosinolates of greater than 50%, 55%, 60%, 65%, 70%, or 75%.

In another embodiment, the present invention provides the process described herein for removing at least one glucosinolate from a meal fraction of a *Brassica carinata* oilseed comprising heating and applying pressure to the oilseed before, during, or after the extraction of oil, wherein the meal proteins are substantially preserved.

In another embodiment, the present invention provides a process for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure.

In another embodiment, the present invention provides the process described herein for removing at least one glucosinolate from a meal fraction of a Brassica carinata oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the temperature of heating in step (a) is greater than 70° C., 75° C., 80° C., 85° C., 90° C., 95° C., 100° C., 105° C., 110° C., 115° C., 120° C., 125° C., 130° C., 135° C., or 140° C., but less than 150° C., 155° C., 160° C., 165° C., 170° C., 175° C., or 180° C.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the duration of heating in step (a) is at least 10, 12, 14, 15, 16, 17, 18, 19, 20, 22, 24, 26, 28, or 30 minutes, but less than 60, 70, 80, 90, or 100 minutes.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process further comprises applying the pressure in step (a) using an expeller or a screw press.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process further comprises applying the pressure in step (a) using an expeller.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process further comprises applying the pressure in step (a) using a screw press.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein step (b) and step (c) occur simultaneously or sequentially.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the time for step (b) and step (c) is greater than 2 min, 5 min, 10 min, 15 min, 20 min, 30 min, 1 h, 2 h, 3 h, or 4 h, and less than 9 h, 10 h, 11 h, or 12 h.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process further comprises regulating the temperature during step (b) and step (c) to prevent the temperature from exceeding 45° C., 50° C., 55° C., 60° C., 65° C., or 70° C.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process further comprises carrying out step (b) and step (c) in a reaction vessel under negative pressure of over 10%, 20%, 30%, 40%, 50%, 60%, 70%, 80%, 90%, 95%, 98%, or 99% vacuum and evacuating volatile substances from the reaction vessel.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process further comprises increasing the temperature to over 60° C., 65° C., 70° C., 75° C., 75° C., 80° C., 80° C., 85° C., 85° C., 85° C., or 90° C. but to less than 95° C., 100° C., 105° C., 110° C., or 115° C., following step (b) and step (c) and further incubating the meal fraction of oilseed until the moisture content of the meal fraction of oilseed decreases to less than 20%, 18%, 16%, 14%, 12%, or 10%.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process further comprises increasing the temperature to over 60° C., 65° C., 70° C., 75° C., 80° C., 85° C., or 90° C., but to less than 95° C., 100° C., 105° C., 110° C., or 115° C., following step (b) and step (c) and further incubating the meal fraction of oilseed until the moisture content of the meal fraction of oilseed decreases to less than 20%, 18%, 16%, 14%, 12%, or 10%; and wherein the process further comprises carrying out the further incubation in a reaction vessel under negative pressure of over 10%, 20%, 30%, 40%, 50%, 60%, 70%, 80%, 90%, 95%, 98%, or 99% vacuum and evacuating volatile substances from the reaction vessel.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process further comprises continuously mixing the meal fraction of oilseed and exogenous myrosinase.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process further comprises preheating the meal fraction of oilseed to between 25° C. to 40° C. prior to step (b).

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process further comprises providing the exogenous myrosinase in the form of a triggering solution comprising a slurry of defatted meal in water.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process further comprises providing the exogenous myrosinase in the form of a triggering solution comprising a slurry of defatted meal in water; and wherein the defatted meal is from oilseed of a plant species of the Brassicaceae family.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process further comprises providing the exogenous myrosinase in the form of a triggering solution comprising a slurry of defatted meal in water; and wherein the defatted meal is from oilseed of *Sinapis alba* or *Brassica carinata*.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process further comprises providing the exogenous myrosinase in the form of a triggering solution comprising a slurry of defatted meal in water; and wherein the triggering solution further comprises ascorbic acid.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process further comprises providing the exogenous myrosinase in the form of a triggering solution comprising a slurry of defatted meal in water; and wherein the process further comprises adding triggering solution to the meal fraction of oilseed in a ratio of 0.5:1, 0.55:1, 0.6:1, 0.65:1, or 0.7:1 (w/w) triggering solution: meal fraction of oilseed.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the meal fraction of oilseed to be treated in steps (b) and (c) is pelleted and homogenized by hammer-milling to a size of less than 5.66 mm, 4.75 mm, 4.00 mm, 3.36 mm, 2.83 mm or 2.38 mm.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the process results in a reduction of glucosinolates of greater than 75%, 80%, 85%, 90%, or 95%.

In another embodiment, the present invention provides the process described herein for removing at least one glucosinolate from a meal fraction of a *Brassica carinata* oilseed comprising: (a) heating and applying pressure to the oilseed before, during, or after the extraction of oil; (b) treating the meal fraction of oilseed with exogenous myrosinase to convert the at least one glucosinolate to a volatile isothiocyanate; and (c) removing the volatile isothiocyanate from the treated meal fraction of oilseed under conditions of mild heat and negative pressure; wherein the meal proteins are substantially preserved.

EXAMPLES

Example 1. Analytical methods for determination of Glucosinolate (GSL) and allyl-isothiocyanate. An HPLC analytical method was adapted from two publications (Cools and Terry, 2012; Berhow et al., 2013). Modifications included mobile phase composition and gradient conditions to allow for analysis of sinigrin and its allyl isothiocyanate degradation product in a single injection. The analytical system was comprised of an Agilent™ 110 HPLC system equipped with a binary pump, autosampler, column compartment and variable wavelength detector, and Chemstation™ control and data acquisition software. The HPLC column utilized was a Waters Xterra™ RP18, 3.5 μm, 4.6×250 mm analytical column and a 20 μL injection volume was used. The detection wavelengths used were 226 nm for sinigrin and 242 nm for allyl-isothiocyanate. Reference standards used were sinigrin (Sigma™ S1647) and allyl-isothiocyanate (Sigma™ 36682). The mobile phases used were Acetonitrile (Phase A) and DI H2O (Phase B). Solvent delivery used a gradient profile as follows; 0-2.5min 99% B, 3-7.5min 30% B, 8.5-10min 99% B with a 1.5 min post-run hold. To investigate the linearity of response, calibrators for sinigrin and allyl-isothiocyanate were prepared at 6 concentrations covering a concentration range from 5-1000 μg/mL (shown below).

| Analyte | Retention Time (min) | Concentration (μg/mL) | Peak Area |
|---|---|---|---|
| Sinigrin | 3.10 | 5 | 41.07 |
| | | 10 | 90.24 |
| | | 50 | 430.26 |
| | | 100 | 839.18 |
| | | 500 | 4129.71 |
| | | 1000 | 8284.68 |
| AITC | 9.14 | 5 | 22.07 |
| | | 10 | 59.66 |
| | | 50 | 218.61 |
| | | 100 | 408.09 |
| | | 500 | 1893.30 |
| | | 1000 | 3948.86 |

Injection of 3 separate preparations of the 6-point calibration curves showed variability of less than 10% for both retention time and peak area. Conditions for extraction of sinigrin from seed meals were determined and optimized and the extracts showed no significant interference at the retention times for either anylate and did not affect peak shape. Extraction parameters developed were 50% aqueous acetonitrile added in a 20:1 ratio to seed meal (e.g. 10 mL solvent to 500 mg seed meal) and placed in boiling water bath in sealed containers for 30 min. The resulting samples were centrifuged, supernatant diluted 1:1 with DI H2O and then again 1:1 with 75% aqueous acetonitrile, and the final solution filtered prior to injection.

Example 2: Preparation of exogenous myrosinase source. Defatted meal from seeds of *Sinapis alba* c.v. Andante or *Brassica carinata* A100 was prepared as follows: 4.5 kg of clean seed was ground using a Waring™ blender at medium speed into a uniform meal (i.e. until no full seeds remained visible). The contents of the blender was emptied into a metal sieving pan and placed on a heating plate set at 80° C. for 20 minutes. During this time the ground seeds were mixed occasionally to prevent charring. The pan was then removed from the heat and allowed to cool at room temperature. 400 mL of ground seed was then placed in a one liter bottle, 200 mL hexane was added and then the capped bottle was hand shaken vigorously. The phases were allowed to separate and the oil phase was removed while the solid meal fraction was re-extracted three additional times with 200 ml hexane as described. After the final extraction, the meal was removed from the bottle and allowed to air-dry in a fume cabinet overnight. The relative myrosinase activity of the defatted meal samples processed as above was estimated by incubating meal samples in the presence of exogenous sinigrin for 3, 5, 10 and 15 minutes, extracting the sinigrin and allyl-isothiocyanate as described in Example 1, and measuring allyl isothiocyanate production via estimation of HPLC peak height. A typical assay is shown in the table below.

| Defatted Meal | Allyl isothiocyanate Peak Area | | | |
|---|---|---|---|---|
| Sample | 3 min | 5 min | 10 min | 15 min |
| *Brassica carinata* | 51 | 61 | 68 | 64 |
| *Brassica carinata* + SG | 91 | 264 | 282 | 284 |
| *Sinapis alba* + SG | 189 | 347 | 291 | 273 |

The results indicate that exogenous sinigrin added to the defatted *Sinapis alba* or *Brassica carinata* meal samples is rapidly converted to allyl-isothiocyanate under the conditions of the assay, confirming the presence of active myrosinase in the processed samples. It should be noted that the conditions used to produce the defatted meal in this example were optimized for maximal oil recovery. Subsequent experiments carried out to optimize conditions for obtaining maximal myrosinase activity have determined that heating of freshly ground meal samples at 50° C. rather than 80° C. results in better preservation of myrosinase activity (data not shown).

Example 3: Assay for glucosinolate reduction from high glucosinolate meal source. A high glucosinolate lot of *Brassica carinata* meal (assayed to contain 100.12 µmol/g total glucosinolate as determined using the International Organization for Standardization method reference number ISO 9167-3: 2007 (E) Rapeseed-13 Determination of glucosinolate content—Part 3: Spectrometric method for total glucosinolates by glucose release) was used to test the ability of the enzyme trigger solution to reduce the glucosinolate level. Samples of this meal were adjusted to various moisture contents by adding the solution of *Sinapis alba* meal (5% in water containing buffer and ascorbic acid). The triggered meal samples were incubated at 55° C. for 30 min and extracted for HPLC analysis of the sinigrin content. As can be seen in the table below, the results show that greater than 80% glucosinolate reduction can be obtained using moisture content and trigger meal concentration that is within the anticipated working range for processing.

| Sample | SG Peak Area | % SG Reduction |
|---|---|---|
| 20% Moisture | 1735 | 55 |
| 25% Moisture | 898 | 77 |
| 30% Moisture | 586 | 85 |
| Control (untriggered) | 3894 | — |

Example 4: Glucosinolate reduction carried out at room temperature. The experiment described in Example 3 was repeated at room temperature using 30% moisture adjustment and compared with the performance of a trigger solution using the *Brassica carinata* meal prepared previously (BC/May) or the *Sinapis alba* meal prepared previously (SA/May). The results, summarized in the table below indicated that the batch of defatted *Brassica carinata* meal, prepared as described in Example 2 for use as a trigger agent, had significant glucosinolate reduction activity. The % SG Reduction is the reduction at 60 min.

| Sample | SG Peak Area (30 min, RT) | SG Peak Area (60 min, RT) | % SG Reduction |
|---|---|---|---|
| 30% Moisture SA/May | 949 | 700 | 82 |
| 30% Moisture BC/May | 1701 | 1552 | 60 |
| Control (untriggered) | 3894 | — | — |

Example 5: Glucosinolate reduction carried out in the absence of buffering agents. Since the meal produced using this process is destined for animal feed it was important to minimize the addition of extraneous chemical compounds to the processing components (i.e. triggering solution). Therefore the activity of the trigger solutions with and without the addition of buffers was assessed. The experiments were carried out using 40% moisture and 60° C. incubation temperature. The results shown in the table below indicate that the activity of the trigger solution when applied to dried meal at a level corresponding to 40% moisture is not strongly dependent on the presence of buffers. The buffer used was 0.1 M potassium phosphate, pH 6.5. The % SG Reduction is the reduction at 60 min.

| Sample | SG Peak Area (30 min, RT) | SG Peak Area (60 min, RT) | % SG Reduction |
|---|---|---|---|
| 40% Moisture SA/May - Buffer + AA | n/a | 136 | 96.5 |
| 40% Moisture SA/May - AA | 182 | 115 | 97 |
| 40% Moisture BC/May - Buffer + AA | n/a | 328 | 91.6 |
| 40% Moisture BC/May - AA | 410 | 410 | 89.5 |
| Control (untriggered) | 3894 | — | — |

Example 6: Glucosinolate reduction under desolventizing and toasting conditions. Since the temperature of the meal in the stage of a typical crushing operation may vary from input press cake temperature of ~50° C. to desolventizing-toasting (DT) operating temperature of 90° C., the activity of the trigger process was assessed using a temperature gradient that would approximate conditions in the DT. An adjusted meal moisture content of 35% was used and the temperature gradient shown in the table below was applied. The results shown below indicate that the trigger solution can theoretically yield glucosinolate reduction of the meal of greater than 75% when applied through the spray nozzle in the desolventizing-toasting equipment that is present in most commercial seed crushing operations.

| Temperature (° C.) | Time (min) |
|---|---|
| 55 | 2 |
| 65 | 3 |
| 75 | 3 |
| 85 | 12 |

| Sample | SG Peak Area | % GLUCs Reduction |
|---|---|---|
| SA/May | 948 | 76 |
| BC/May | 1528 | 61 |
| Control (untriggered) | 3894 | — |

Example 7: Pretreatment of meal prior to glucosinolate reduction. The assayed value of glucosinolate in large scale was obtained from a batch that was initially in a pellet form. Hammer milling was carried out on the carinata meal samples to produce a uniform particle size prior to batch processing in a Littleford™ dryer. The hammer milling was carried out in a mill equipped with a ⁵⁄₆₄" screen (Model G5HFS1, serial number 5075, Prater Industries, Chicago Ill.). Hammer-milled carinata meal was dried to <12% moisture and then packaged into bulk sacks prior to glucosinolate removal processing.

Example 8: Batchwise processing of meal for glucosinolate reduction: 13 batches of hammer-milled carinata meal samples were individually processed to remove glucosinolates as described below. The batch characteristics are as described in the tables below. For each batch process approximately 200 kg of meal was loaded into the Littleford™ vacuum dryer (Littleford Reactor™ 600 liter model FKM600-D 2Z, serial number 5132, Littleford-Day Inc., Florence, KY). FIG. 2 is a schematic diagram of the apparatus used for the batchwise removal of glucosinolate from Brassica carinata meal. The large dash box (a) indicates the Littleford vacuum dryer apparatus, which includes the reaction vessel 2 for the batchwise treatment of meal for removal of glucosinolates. The plough mixer was started and the meal heated to 35° C. 120 kg of soft water was loaded into a 200 liter stainless steel mixing vessel 6 and 45 g of ascorbic acid was added. The dashed box in the lower right hand corner (b) indicates the mixing vessel 4 where the triggering solution is prepared. After 5 minutes of mixing, 5 kg of defatted Sinapis alba meal (batches 1-12) or Brassica carinata meal (batch 13) was added to the mixing vessel 4 to form the triggering solution. The triggering solution was circulated via the inline mixer, comprising piping 20 attached to a recirculation pump 22 downstream of drain 24, for 20 minutes and then sprayed into the Littleford™ dryer reaction vessel 2 where it was allowed to react with the carinata meal for 3 hours. In batch one, after the three hour reaction, a vacuum 46 was applied to the reaction vessel 2 and the meal was heated to 50° C. for one hour. After the one hour hold at 50° C., the meal was heated to 70° C. -74° C. and dried to a moisture content of <12%. During batch one processing it was noted that the reaction was highly exothermic, so it was decided to remove the 1 hour hold at 50° C. and, instead, cooling water was circulated in the dryer jacket (not visible) from the outset of the reaction to allow attainment of a maximum temperature at 50° C. -60° C. during the three hour reaction. From batch five onwards this was further modified so that cooling water was applied only once the temperature in the reaction vessel 2 had reached 35° C. during the initial reaction. Also from batch 3 onwards, vacuum was applied from the onset of the initial reaction. Once the processing for all batches was completed, small samples were removed for sinigrin peak height assay, while the remainder was packaged for storage. Samples of meal taken from the individual processed batches were individually extracted and analyzed by HPLC as described in Example 1. The data of this analysis is summarized in the table below.

| Batch # | SG Peak Area Starting Material* | SG Peak Area of Treated Final Product | % SG Reduction |
|---|---|---|---|
| 1 | 4247 mean | 482 | 88.65 |
| 2 | 4247 mean (2735 actual) | 489 | 88.49 (82.12) |
| 3 | 4247 mean | 482 | 88.65 |
| 4 | 4247 mean | 496 | 88.32 |
| 5 | 4247 mean | 507 | 88.06 |
| 6 | 4247 mean | 490 | 88.46 |
| 7 | 4247 mean | 462 | 89.12 |
| 8 | 4247 Avg (5027 actual) | 489 | 88.49 (90.27) |
| 9 | 4247 mean | 499 | 88.25 |
| 10 | 4247 Avg (4979 actual) | 496 | 88.32 (90.04) |
| 11 | 4247 mean | 504 | 88.13 |
| 12 | 4247 mean | 512 | 87.94 |
| 13 (BC)** | 4247 mean | 501 | 88.20 |

*Starting material samples were only provided for batches 2, 8, and 10.
**Meal used in trigger solution was Brassica carinata produced in the AGS lab As can be seen, all processed batches gave greater than 80% reductions in levels of glucosinolates relative to the starting material. Similar reductions were observed in batches 1 through 12, indicating that the heat generated by the exothermic reaction is sufficient to drive the process and that cooling only needed to be applied to keep the reaction temperature from exceeding the 50° C.-60° C. ceiling. As well, it was also apparent that Brassica carinata based triggering solution was equivalent to Sinapis alba based triggering solution in terms of its ability to catalyze the conversion of the glucosinolates.

Example 9. HPLC analysis of total GLS content samples of carinata meal. Quantitative HPLC analysis of meal samples were carried out on meal samples prepared from commercial carinata variety A110 essentially as described in Berhow et al., 2013. The meal samples consisted of: sample 1: defatted meal prepared from A110 Brassica carinata seed as described in example 2; samples 2,3: meal from a commercial crush of A110 Brassica carinata seed processed via hexane extraction as described in the background section; samples 4,5: meal from a commercial crush of A110 seed and further processed as described in Example 8.

| Sample ID | uM/g GTRO DF | uM/g SINIG DF | uM/g SINA DF | uM/g GNAP DF | uM/g GNAS DF |
|---|---|---|---|---|---|
| 1 A110 Carinata A (defatted meal) | 0.00 | 68.72 | 0.00 | 5.15 | 0.38 |
| 2 A_1AP_A Pelleted | 0.00 | 13.13 | 0.00 | 0.00 | 0.00 |
| 3 A_3BP_A Pelleted | 0.00 | 18.75 | 0.91 | 4.19 | 0.00 |
| 4 P_B6/7_A | 0.00 | 0.00 | 0.00 | 0.00 | 0.00 |
| 5 P_B8/9_A | 0.00 | 0.00 | 0.00 | 0.00 | 0.00 |

In the above table, GTRO is progoitrin, Sinig is Sinigrin, Sina is Sinalbin, GNAP is gluconapin, and GNAS is gluconasturtin. These molecules are the different glucosinolates present in the meal samples.

As can be seen in the above table, meal prepared from seed crushed and defatted in a lab scale process described in Example 2 (sample 1) performed with minimal heating during the procedure contained appreciable levels of glucosinolates consisting mainly of sinigrin (with lesser amounts of gluconapin and gluconasturtin). Meal of the same seed variety but prepared from a commercial seed crush (samples 2, 3) where the cooking and flaking were carried out at elevated temperatures (greater than 105° C.) showed significant (68%-82%) reduction in glucosinolate levels relative to sample 1, whereas glucosinolate levels of meal of the same seed variety obtained from a commercial crush and further processed using the procedure described in Example 8 (samples 4, 5) were further reduced such that any remaining glucosinolate was below the limit of detection of the assay.

Example 10: Cooking flaked carinata oilseed. In a research scale crush carried out on carinata A110 seed, a cooking step was employed on the flaked seeds which comprised heating at 70° C. to 93° C.

Cooking is a standard practice carried out on the flaked seed whereby the flakes are passed through stack-type cookers to disrupt oil cells that have survived flaking, reduce oil viscosity, denature hydrolytic enzymes and myrosinase, and adjust the moisture of the flakes prior to pressing. Temperatures for cooking typically range from 80-105° C.

For the crush, the temperature was rapidly increased to 93° C. and the cycle was maintained for 15-20 minutes. The flaked carinata seeds then underwent crushing using an expeller, followed by hexane extraction to recover residual oil, followed by desolventing and toasting steps as previously described. The carinata meal produced by this process was found to have glucosinolate levels in the range of 110-120 µmol/g.

Example 11: Cooking flaked carinata oilseed at elevated temperatures. In a subsequent crush carried out by a commercial crusher, cooking was carried out on flaked carinata seed as described above, except that the temperature of the cooking step exceeded 110° C., 115° C. or 120° C. At these temperatures, significant thermal degradation of glucosinolates occur, and indeed the meal produced by this crush was found to contain glucosinolate levels of 13-20 µmol/g, significantly less than what was obtained with the lower cooking temperature of the processing.

Meal obtained through a commercial crush as described in the previous paragraph was subsequently processed by batchwise treatment with an exogenous source of myrosinase (see Examples 7 and 8). The resultant meal was shown to contain levels of glucosinolates that were below the levels of detection of the HPLC based assay (see table in Example 9).

REFERENCES

Anderson-Hafermann, J. C., et al. (1993). "Effects of Processing on the Nutritional Quality of Canola Meal." Poultry Science 72: 326-333.

Aumaitre, A., et al. (1989). "Effect of Graded Levels of Raw and Processed Rapeseed on Feed Digestibility and Nutrient Utilization in Young Pigs." Animal Feed Science and Technology 24: 275-287

Bellostas, N., et al. (2004). "Qualitative and quantitative evaluation of glucosinolates in cruciferous plants during their life cycles." Agroindustria 3(3): 5-10.

Berhow, M. A., et al. (2013). "Optimized analysis and quantification of glucosinolates from Camelina sativa seeds by reverse-phase liquid chromatography." Industrial Crops and Products 43: 119-125.

Blackshaw R E, Johnson E N, Gan Y, May W E, McAndrew D W, Barthet V, McDonald T, Wispinski D. (2011). Alternative oilseed crops for biodiesel feedstock on the Canadian prairies. Can. J. Plant. Sci. 91:889-896.

Bones, A. M. (1990). Distribution of beta-thioglucosidase activity in intact plants, cell and tissue cultures and regenerated plants of Brassica napus L. J. Exp. Bot. 41: 737-744.

Bouaid A, Diaz Y, Martinez M, Aracil J. 2005. Pilot plant studies of biodiesel production using Brassica carinata as raw material. Catalysis Today 106(1-4):193-196.

Branca, F. and E. Cartea (2011). Brassica. Wild Crop Relatives: Genomic and Breeding Resources, Oilseeds. C. Kole. Berlin Heidelberg Springer-Verlag 17-36.

Cardone M, Prati M V, Rocco V, Seggiani M, Senatore A, Vitolo S. (2002). Brassica carinata as an alternative oil crop for the production of biodiesel in Italy: engine performance and regulated and unregulated exhaust emissions. Environ. Sci. Technol. 36:4656-4662.

Cardone M, Mazzoncini M, Menini S, Rocco V, Senatore A, Seggiani M, Vitolo S. (2003). Brassica carinata as an alternative oil crop for the production of biodiesel in Italy: Agronomic evaluation, fuel production by transesterification and characterization. Biomass and Bioenergy 25(6):623-636.

Cools, K. and Terry, L. A. (2012). "Comparative study between extraction techniques and column separation for the quantification of sinigrin and total isothiocyanates in mustard seed." J. Chromatogr. B 901: 115-118.

Drenth, A. C., et al. (2014). "Compression ignition engine performance and emission evaluation of industrial oilseed biofuel feedstocks camelina, carinata, and pennycress across three fuel pathways." Fuel 136(0): 143-155.

Drenth, A. C., et al. (2015). "Fuel property quantification of triglyceride blends with an emphasis on industrial oilseeds camelina, carinata, and pennycress." Fuel 153: 19-30.

Dai, R. and L.-T. Lim (2014). "Release of Allyl Isothiocyanate from Mustard Seed Meal Powder." Journal of Food Science 79(1): E47-E53.

Fahey, J. W., et al. (2001). "The chemical diversity and distribution of glucosinolates and isothiocyanates among plants." Phytochemistry 56: 5-51.

Fenwick, G. R., et al. (1986). "Effect of Processing on the Antinutrient Content of Rapeseed." I. Sci. Food Agric. 37: 735-741.

Gasol C M, Gabarrell X, Anton A, Rigola M, Carrasco J, Ciria P, Solano M L, Rieradevall J. (2007). Life cycle assessment of a Brassica carinata bioenergy cropping system in southern Europe. Biomass and Bioenergy 31:543-555.

Gasol C M, Gabarrell X, Anton A, Rigola M, Carrasco J, Ciria P, Rieradevall J. (2009). LCA of poplar bioenergy system compared with Brassica carinata energy crop and natural gas in regional scenario. Biomass and Bioenergy 33:119-129.

Getinet A. (1986). Inheritance of seed coat colour in Brassica carinata A. Braun and an examination of seed quality parameters and their transfer from related species (B. napus L. and B. juncea Czern & Coss). M. Sc. Thesis, Department of Crop Science and Plant Ecology, University of Saskatchewan, Saskatoon, SK. 105 pp.

Getinet A, Rakow G, Downey R K. (1996). Agronomic performance and seed quality of Ethiopian mustard in Saskatchewan. Canadian Journal of Plant Science 76(3): 387-392.

Halkier, B. A. and J. Gershenzon (2006). "Biology and biochemistry of glucosinolates." Annual Review of Plant Biology 57(1): 303-333.

Henderson, H. M. and McEwen, T. J. (1972). Effect of ascorbic acid on thioglucosidases from different crucifers. Phytochemistry 11: 3127-3133.

Kissen, R., Rossiter, J. T. and Bones, A. M. (2009). "The 'mustard oil bomb': not so easy to assemble?! Localization, expression and distribution of the components of the myrosinase enzyme system." Phytochemistry Reviews 8(1): 69-86.

Mavromichalis, I. (2001). "The Maillard reaction in feed manufacturing." Feed Tech 5(2): 13-14).

Marillia E-F, Francis F, Falk K C, Smith M and Taylor D C (2014). "Palliser's promise: Brassica carinata, An emerging western Canadian crop for delivery of new bio-industrial oil feedstocks." Biocatalysis and Agricultural Biotechnology 3(1): 65-74.

Nagaharu, N. (1935). Genome analysis in Brassica with special reference to the experimental formation of B. napus and peculiar mode of fertilization. Japan J. Bot. 7:389-452.

Prakash S, Wu X-M, Bhat SR. (2012). History, Evolution and Domestication of Brassica crops. In: Plant Breeding Reviews. Janick J (ed). Vol. 35.19-84.

Rask, L, et al. (2000). "Myrosinase: gene family evolution and herbivore defense in Brassicaceae." Plant Molecular Biology 42: 93-113.

Taylor D C, Falk K C, Palmer C D, Hammerlindl J, Babic V, Mietkiewska E, Jadhav A, Marillia E F, Francis T, Hoffman T, Giblin E M, Katavic V, Keller W A. (2010). *Brassica carinata*—A new molecular farming platform for delivering bio-industrial oil feedstocks: Case studies of genetic modifications to improve very long-chain fatty acid and oil content in seeds. Biofuels, Bioproducts and Biorefining 4(5):538-561.

Tripathi, M. K. and A. S. Mishra (2007). "Glucosinolates in animal nutrition: A review." Animal Feed Science and Technology 132(1-2): 1-27.

van Megen, W. H. U.S. Pat. No. 4,244,973 "Process for producing a detoxified rapeseed protein concentrate".

Warwick S I, Francis A, Gugel R K. (2009). Guide to Wild Germplasm of *Brassica* and Allied Crops (tribe Brassiceae, Brassicaceae), 3$^{rd}$ Edition. PART III. Interspecific and intergeneric hybridization data. [Online] Available: https://brassica.info/info/publications/guidewild/Guide_ed3_Introd_16July2006.pdf. Accessed 20 Nov 2014.

Xin, H., et al. (2014). "Mid-Infrared Spectral Characteristics of Lipid Molecular Structures in Brassica carinata Seeds: Relationship to Oil Content, Fatty Acid and Glucosinolate Profiles, Polyphenols, and Condensed Tannins." Journal of Agricultural and Food Chemistry 62(32): 7977-7988.

The invention claimed is:

1. An animal feed additive comprising a meal fraction produced from *Brassica carinata* oilseed, wherein said meal fraction comprises less than 20 µmol total glucosinolates per gram of meal and is produced by a process comprising:
   - obtaining *Brassica carinata* oilseed comprising between about 60 and about 100 µmol total glucosinolates per gram of oilseed in which sinigrin constitutes more than 90% of the total glucosinolate content of the *Brassica carinata* oilseed;
   - pressing the *Brassica carinata* oilseed to produce oilseed flakes;
   - cooking the oilseed flakes at a temperature in the range of 105° C. to 120° C. for a period of 10 to 100 minutes;
   - pressing the cooked oilseed flakes to remove oil from the oilseed flakes, thereby producing an oil fraction and a meal fraction;
   - treating the meal fraction with hexane to extract residual oil;
   - desolventizing-toasting the hexane-extracted meal fraction to remove residual hexane for a period of greater than 1 hour but less than 5 hours;
   - drying the meal fraction to a moisture content of 12% or less, and recovering a meal fraction of *Brassica carinata* having a total glucosinolates content of less than 20 µmol per gram of meal.

2. The animal feed additive of claim 1, wherein cooking the oilseed flakes comprises cooking the oilseed flakes at a temperature in the range of 110'C to 120° C. for a period of 15 to 20 minutes.

3. The animal feed additive of claim 1, wherein the meal fraction produced from the *Brassica carinata* oilseed comprises less than 15 µmol sinigrin per gram of meal.

4. The animal feed additive of claim 1, wherein the meal fraction produced from the *Brassica carinata* oilseed comprises less than 15 µmol total glucosinolates per gram of meal.

5. The animal feed additive of claim 1, wherein the meal fraction produced from the *Brassica* carinata oilseed is pelleted and homogenized by hammer—milling to a size of less than 5.66 mm.

6. The animal feed additive of claim 1, wherein cooking the oilseed flakes comprises cooking the oilseed flakes for a period of 90 to 100 minutes.

7. A feed ration comprising the animal feed additive of claim 1.

8. The feed ration of claim 7, wherein the feed ration is suitable for ruminant livestock, monogastric livestock, or poultry livestock.

9. The feed ration of claim 8, wherein the ruminant livestock is cattle.

10. The feed ration of claim 9, wherein the feed ration is formulated to maximize weight gain and meat quality of beef cattle in the feed lot, or to maximize milk production of lactating dairy cattle.

11. The feed ration of claim 8, wherein the monogastric livestock is swine.

12. The feed ration of claim 7, further comprising dried distiller grains.

* * * * *

UNITED STATES PATENT AND TRADEMARK OFFICE
CERTIFICATE OF CORRECTION

| | | |
|---|---|---|
| PATENT NO. | : 11,889,850 B2 | Page 1 of 1 |
| APPLICATION NO. | : 17/243695 | |
| DATED | : February 6, 2024 | |
| INVENTOR(S) | : Mark Hetherington et al. | |

It is certified that error appears in the above-identified patent and that said Letters Patent is hereby corrected as shown below:

On the Title Page

Item (73) Assignee: Remove "AGRISOMA BIOSCIENCES INC., Gatineau (CA)", and add "NUSEED GLOBAL INNOVATION LTD., Manchester (UK)".

Signed and Sealed this
Tenth Day of June, 2025

Coke Morgan Stewart
*Acting Director of the United States Patent and Trademark Office*